(12) United States Patent
Heaven et al.

(10) Patent No.: US 11,895,953 B2
(45) Date of Patent: Feb. 13, 2024

(54) PLANT HEALTH MONITORING APPARATUS AND METHODS

(71) Applicant: ARGUS CONTROL SYSTEMS LTD., Surrey (CA)

(72) Inventors: Edwin Michael Gyde Heaven, North Vancouver (CA); Donny Cayanan, Langley (CA)

(*) Notice: Subject to any disclaimer, the term of this patent is extended or adjusted under 35 U.S.C. 154(b) by 265 days.

(21) Appl. No.: 17/614,360

(22) PCT Filed: May 31, 2020

(86) PCT No.: PCT/CA2020/050747
§ 371 (c)(1),
(2) Date: Nov. 25, 2021

(87) PCT Pub. No.: WO2020/237395
PCT Pub. Date: Dec. 3, 2020

(65) Prior Publication Data
US 2022/0256789 A1 Aug. 18, 2022

Related U.S. Application Data

(60) Provisional application No. 62/855,641, filed on May 31, 2019.

(51) Int. Cl.
*A01G 25/16* (2006.01)
*A01G 7/04* (2006.01)
(Continued)

(52) U.S. Cl.
CPC ........ *A01G 25/167* (2013.01); *G01N 21/3563* (2013.01); *G01N 33/0098* (2013.01); *G05B 19/042* (2013.01); *G05B 2219/2625* (2013.01)

(58) Field of Classification Search
CPC ......... A01G 7/045; A01G 9/24; A01G 25/167
See application file for complete search history.

(56) References Cited

U.S. PATENT DOCUMENTS 3,614,450 A 10/1971 Hill et al.
4,301,682 A 11/1981 Everest
(Continued)

FOREIGN PATENT DOCUMENTS

CA 3020268 A1 10/2018
CN 102426153 A 4/2012
(Continued)

OTHER PUBLICATIONS

Zhai et al., "Estimation of nitrogen, phosphorus, and potassium contents in the leaves of different plants using laboratory-based visible and near-infrared reflectance spectroscopy: comparison of partial lease-square regression and support vector machine regression models". International Journal of Remote Sensing, Oct. 4, 2013 (Apr. 10, 2013), vol. 34 (7), pp. 2502-2518, ISSN 1366-5901.
(Continued)

*Primary Examiner* — Monica L Perry

(57) ABSTRACT

Methods and apparatus for determining a plant health parameter based on a measured IR parameter of the plant are provided. If the measured plant health parameter indicates the plant is experiencing a stress condition, an alert can be provided and/or a control system can be activated to supply environmental elements such as water to the plant to ameliorate the stress condition.

20 Claims, 16 Drawing Sheets

(51) Int. Cl.
*G01N 21/3563* (2014.01)
*G01N 33/00* (2006.01)
*G05B 19/042* (2006.01)

(56) References Cited

U.S. PATENT DOCUMENTS

| | | | |
|---|---|---|---|
| 4,306,151 | A | 12/1981 | Chase |
| 5,795,394 | A | 8/1998 | Belotserkovsky et al. |
| 2010/0111369 | A1 | 5/2010 | Lussier |
| 2017/0030877 | A1 | 2/2017 | Miresmailli et al. |
| 2021/0251153 | A1* | 8/2021 | Song ............. A01G 7/045 |
| 2022/0062338 | A1* | 3/2022 | Woodard ............ C12N 5/0636 |

FOREIGN PATENT DOCUMENTS

| | | |
|---|---|---|
| CN | 104749134 A | 7/2015 |
| IN | 101936882 A | 1/2011 |
| WO | 2008068699 A1 | 6/2008 |

OTHER PUBLICATIONS

Spectral Properties of Leaves & Plants, University of California Davis, online <http://cstars.metro.ucdavis.edu/files/3613/4419/0702/Lecture_3-Leaves_Plants.pdf>, accessed May 28, 2020.

Abscisic acid, PubChem Compound Summary. Available at least as early as May 27, 2020.

Multispectral Imaging Camera Drones in Farming Yield Big Benefits, Dronezon, online <https://www.dronezon.com/ earn-about-drones-quadcopters/multispectral-sensor-drones-in-farming-yield-big-benefits/>, accessed Apr. 7, 2019.

Vibrational Spectroscopy Tutorial: Sulfur and Phosphorus, online <https://faculty.missouri.edu/~glaserr/8160f10/ A03_Silver.pdf.pdf>, accessed May 28, 2020.

Miller and Wilkins, "Infrared Spectra and Characteristic Frequencies of Inorganic Ions Their Use in Qualitative Analysis", Analytical Chemistry 24(8), Aug. 1952, pp. 1253-1294.

* cited by examiner

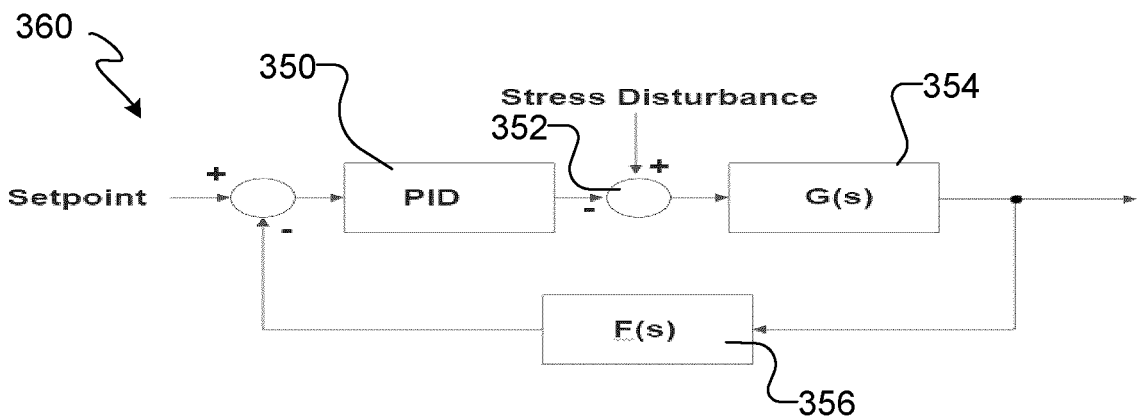
FIG. 9B
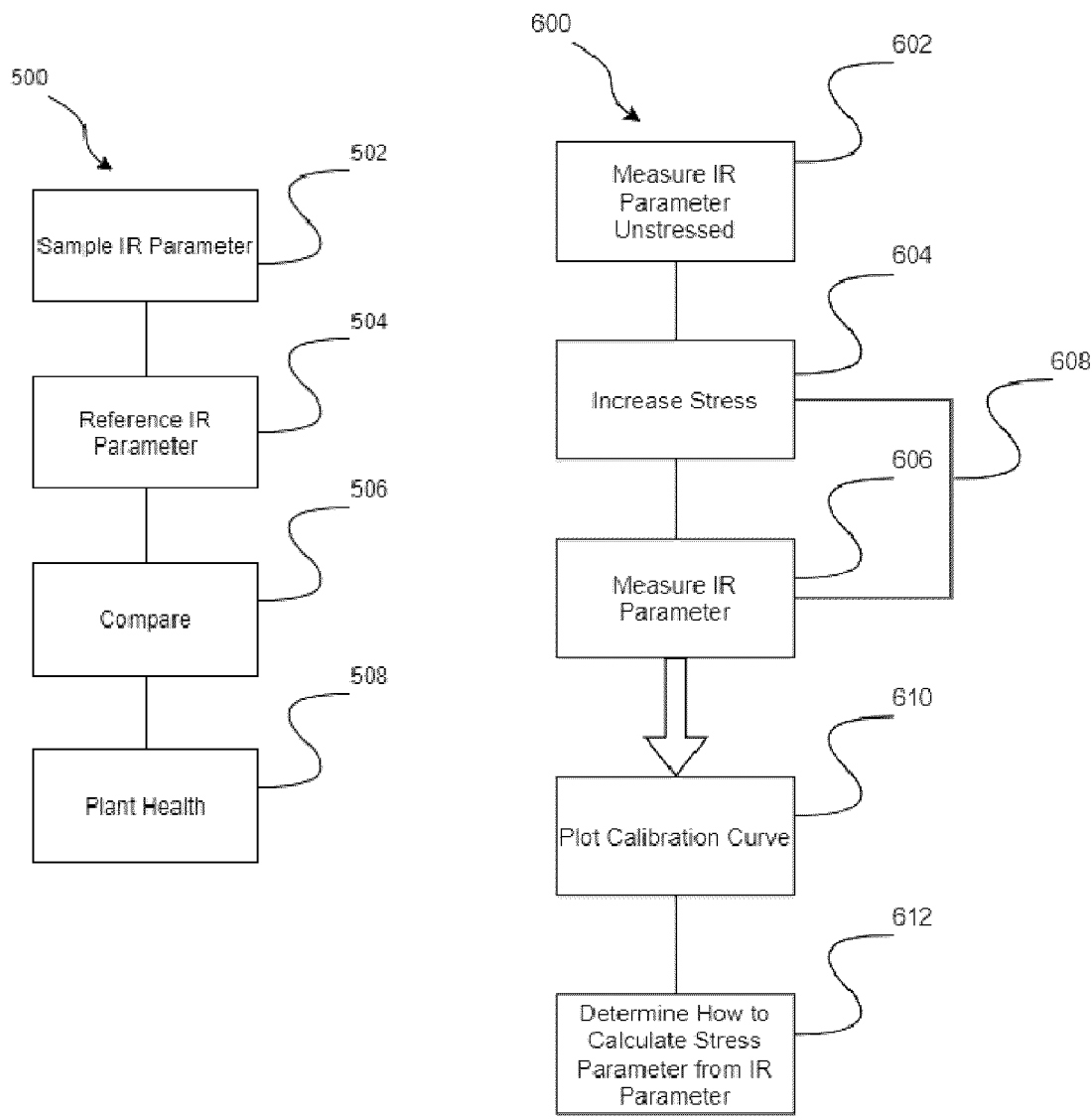
FIG. 10
FIG. 11

Fresh Leaf (100%)

First Leaf out from Oven (36.1%)

Second Leaf out from Oven (26.7%)

Third Leaf out from Oven (12.6%)

Fourth Leaf out from Oven (7.15%)

Fifth Leaf out from Oven (0.31%)

Last Leaf out from Oven (0%)

Fresh Leaf (100%)

First Leaf out from Oven (29.1%)

Second Leaf out from Oven (16.4%)

Third Leaf out from Oven (14.9%)

Fourth Leaf out from Oven (12.3%)

Fifth Leaf out from Oven (1.38%)

Last Leaf out from Oven (0%)

Fresh Leaf (100%)

First Leaf out from Oven (25.8%)

Second Leaf out from Oven (22.7%)

Third Leaf out from Oven (21.1%)

Fourth Leaf out from Oven (20.1%)

Fifth Leaf out from Oven (17.7%)

Last Leaf out from Oven (0%)

PLANT HEALTH MONITORING APPARATUS AND METHODS

CROSS-REFERENCE TO RELATED APPLICATIONS

This application is a 371 national phase entry of PCT application No. PCT/CA2020/050747 filed 31 May 2020, which claims priority to, and the benefit of, U.S. provisional patent application No. 62/855,641 filed 31 May 2019. Both of the foregoing applications are incorporated by reference herein in their entireties for all purposes.

TECHNICAL FIELD

Some embodiments of the present invention pertain to apparatus or methods for monitoring plant health. Some embodiments of the present invention pertain to apparatus or methods that can be used to monitor plant health and adjust growing conditions such as irrigation, light, temperature, carbon dioxide levels and the like, to maintain plant health within a desired range of parameters.

BACKGROUND

It is known that infrared energy is absorbed by different materials at different wavelengths (infrared spectroscopy). As used herein, the term "infrared" may be referred to by its abbreviation "IR".

The level of a component in a material may be measured by comparing spectral properties of the sample at a wavelength at which the component exhibits specific properties (e.g. a wavelength at which the component absorbs infrared radiation to a significant extent) with a reference property, such as the spectral properties of the material at a wavelength at which the component exhibits control properties (e.g. a wavelength at which the component does not absorbs infrared radiation or absorbs infrared radiation only to a minor degree).

For example, U.S. Pat. No. 3,614,450 illustrates how the moisture content in paper can be measured using infrared energy emitted at two different wavelengths—one that is not absorbed by moisture (centered at 1.8 microns) and one that is absorbed by moisture (centered at 1.94 microns).

U.S. Pat. No. 4,306,151 teaches a method of measuring the amount of substance within a material in the presence of a contaminant, and more particularly, a method of measuring the amount of water associated with paper in the presence of carbon. The amount of moisture is calculated based on two bands—one at 1.8 microns not sensitive to moisture (N) and one sensitive to moisture at 1.94 microns (M). The amount of moisture is determined by Equation (1):

$$\text{Amount of moisture} = A + B^*(M+1/M) + C^*(N+1/N) \quad (1)$$

Where A, B and C are determined from initial calibration using defined moisture level samples.

In U.S. Pat. No. 5,795,394, a method of measuring the coating material on a substrate is taught using infrared wavelengths between 3.6 and 4.2 microns which are sensitive to the coating material ($CaCO_3$) but not sensitive to the underlying properties of the substrate (clay, water, latex and other pigments and fillers). The infrared energy that reflects off the surface is measured as well as the energy that passes through the coating and substrate material and filters are used to separate the resulting signals into wavelengths sensitive to the coating material and wavelengths insensitive to the coating material.

Some aspects of measuring the moisture content of a plant canopy using near infrared image analysis have been disclosed (e.g. CN104749134A), as has a non-destructive testing method of measuring the nitrogen and water content of plant material using infrared temperature (CN101936882A). CN102426153A discloses the measurement of wheat plant moisture content based on spectral reflectance in different energy bands.

U.S. Pat. No. 4,301,682 teaches the use of an infrared thermometer to measure the moisture stress in a plant to determine the watering frequency.

FIG. 1 illustrates the absorption bands of water and also shows the high reflectance of vegetation in the near IR bands. Water exhibits a high degree of absorption at a wavelength in the region of 1940 nm, but minimal absorption at a wavelength in the region of 1700 nm. The IR absorption bands for other components of plants are known, for example as summarized in the table below. Further reference may be had, for example, to the PubChem entry for abscisic acid, published by the National Institutes of Health, "Infrared Spectra and Characteristic Frequencies of Inorganic Ions" by Miller and Wilkins, Anal. Chem., 1952, 24(8):1253-1294, "Spectral Properties of Leaves & Plants", accessed online <http://cstars.metro.ucdavis.edu/files/3613/4419/0702/Lecture_3-Leaves_Plants.pdf>, and "Vibrational Spectroscopy Tutorial: Sulfur and Phosphorus", accessed online <https://faculty.missouri.edu/~glaserr/8160f10/A03_Silver.pdf>.

| Element | Dominant Bond/ Component | IR Absorption Band |
| --- | --- | --- |
| Nitrogen | C—N | 7.4 to 10 microns |
| Phosphorus | P—$CH_3$ | 7000 to 8000 nm |
| Potassium | K+ | 2450 and 2470 nm |
| Abscisic Acid ($C_{15}H_{20}O_4$) | O—H | 5800 and 6250 nm |
| Cellulose/Plant/Leaf Materials | Scattering of near IR due to spongy Mesophyll | 800-1300 nm |
| Chlorophyll | Visible absorption | 400-800 nm |

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect, a method of determining a health parameter of a plant is provided. An infrared (IR) parameter of the plant is measured and compared to a reference value to correlate the measured IR parameter to the health parameter. In some aspects, the reference value is an empirically determined standard curve prepared by correlating the measured IR parameter to the health parameter of the plant at a plurality of different plant stress levels. In some aspects, the reference value is a value determined at a control wavelength at which the measured IR parameter exhibits no or limited variation with variations in plant health. In some aspects, the measured IR parameter is determined at a wavelength at which the measured IR parameter is sensitive to variations in the plant health parameter. In some aspects, the measured IR parameter is determined across a first path having a first length and the reference value corresponds to the measured IR parameter determined across a second path having a second length, the first and second lengths being approximately equal and the first path containing the sample of interest (such as a plant, a plant canopy, or a plant part such as a leaf) while the second path extends through air only.

In some aspects, the health parameter of the plant is biomass, cellulose content, water content, or a level of a compound that is indicative of stress. In some aspects, the health parameter of the plant is a level of one or more of water, nitrogen, phosphorus, potassium, abscisic acid cellulose and/or chlorophyll. In some aspects, the plant health parameter is percentage water content, and the reference value is a standard curve prepared by measuring the IR parameter for a plurality of leaves or plants at a plurality of different known moisture contents.

In some aspects, a method of controlling environmental conditions based on plant heath is provided. Any method as described above or herein is carried out to determine a health parameter of a plant. The plant health parameter is evaluated to determine whether the plant health parameter indicates the plant is experiencing a stress condition. If it is determined that the plant is experiencing a stress condition, a perceptible indication (e.g. visible such as an indicator light or a moving dial on an indicator panel, or audible such as a tone, horn or siren) is provided to alert a user to the fact that the plant is experiencing a stress condition, and/or a controller can be activated to supply one or more elements to the plant to ameliorate the stress condition. In some aspects, a controller can be activated to activate an irrigation system to supply water to the plant. In some aspects, the controller is a proportional-integral-derivative controller that can evaluate further feedback based on continued measurement of the plant health parameter and adjust the supply or elements to the plants accordingly (e.g. by reducing or stopping irrigation to the plants once a water shortage stress condition has been ameliorated).

In some aspects, an apparatus for measuring a plant health parameter is provided. The apparatus has a measuring IR source and a measuring IR detector. The IR source and the measuring IR detector can be mounted on a synchronized linear positioning system. The measuring IR source can be mounted on a first linear actuator capable of movement in a vertical direction, and the measuring IR detector can be mounted on a second linear actuator capable of movement in the vertical direction. The measuring IR source can be mounted on a third linear actuator capable of movement in a horizontal direction, and the measuring IR detector can be mounted on a fourth linear actuator capable of movement in the horizontal direction. In some aspects, the apparatus further has a reference IR source and a reference IR detector that is positioned to determine a reference IR parameter.

In some aspects, the apparatus has a processor that executes a function to compare a measured plant health parameter determined by the apparatus for measuring the plant health parameter. In some aspects, the apparatus comprises a proportional-integral-derivative controller for regulating the supply of environmental elements such as water, light and/or carbon dioxide to the plants. The proportional-integral-derivative controller is configured to receive the plant health parameter output by the system for measuring the plant health parameter, and is also configured to control the operation of at least one of an irrigation supply system for supplying water to the plants, a lighting supply system for supplying light to the plants, a humidity control system for regulating humidity in the air around the plants, and/or a carbon dioxide supply system for supplying carbon dioxide to the plants.

In some aspects, the apparatus or method is non-destructive, i.e. a growing plant is not harmed or destroyed by carrying out the method or using the apparatus.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 9B shows an apparatus that can be used to carry out the method shown in FIG. 9A.

FIG. 10 shows an example embodiment of a method for using an IR parameter to make evaluations of plant health.

FIG. 11 shows an example embodiment of a method for empirically determining a calibration curve so that a measured IR parameter of interest can be converted to a quantitative assessment of plant health or a plant health parameter.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

A non-destructive method of measuring the plant canopy moisture content, biomass, and/or abiotic stress to optimize performance in a controlled plant growth environment using infrared (IR) sources and detectors is disclosed. In one embodiment, the infrared sources emit a beam of infrared energy which passes through the air only in a first path, and through the air and plant canopy in a second, separate, path. In some embodiments, the length of the first and second paths is approximately the same. The infrared sources can be derived from one infrared source split into two beams of equal power. The moisture content of the air can be compared to the moisture content and/or biomass of the plant canopy; from this, the plant canopy moisture content and/or plant biomass can be calculated.

This method exploits the fact that molecules absorb radiation frequencies that are characteristic of their molecular structure. As a result, based on an observed increase in light absorption at frequencies unique to water ($H_2O$) and/or other indicators of plant health such as abscisic acid (ABA), potassium ($K^+$), nitrogen (N), phosphorous (P), cellulose, biomass, chlorophyll and the like, infrared radiation can be used for the measurement of moisture content and/or early detection of the onset of abiotic stress in one or more plants.

Using these non-destructive plant measurements (e.g., moisture content, biomass and/or indicators of abiotic stress), an improved control system is disclosed to optimize the performance of the plant output, leading to an increase in yield and reduction in cost from resource use (e.g. water, carbon dioxide and/or light energy). In some embodiments, the IR source and detector that measure the plant canopy can move vertically up and down to scan the canopy to obtain an average measurement of moisture content, biomass and/or stress of the canopy as well as to move with the plants as they grow. The system can be expanded to move the canopy measurement apparatus horizontally from side to side to accommodate different rows of plants and/or vertically to scan multiple tiers of plants that are often present in a growth chamber.

Figure 1:
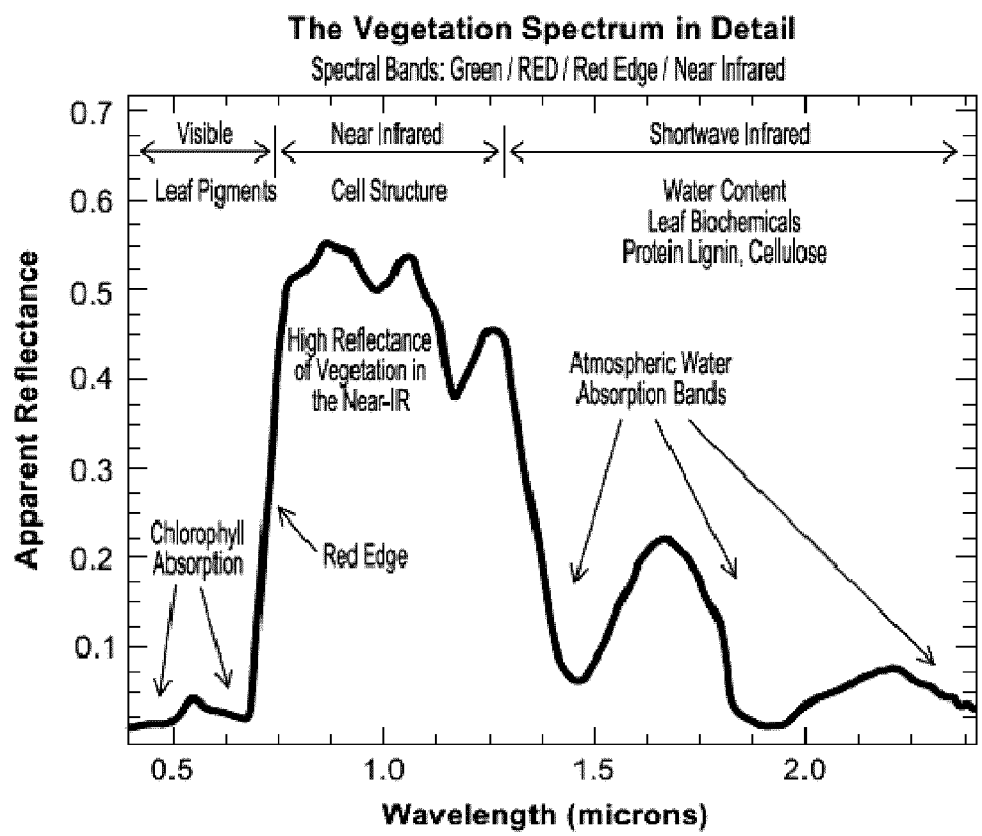
FIG. 1 shows the absorption bands of water in the shortwave infrared region, the high reflectance of vegetation in the near infrared region, and chlorphyll absorption in the visible spectrum.
Figure 2:
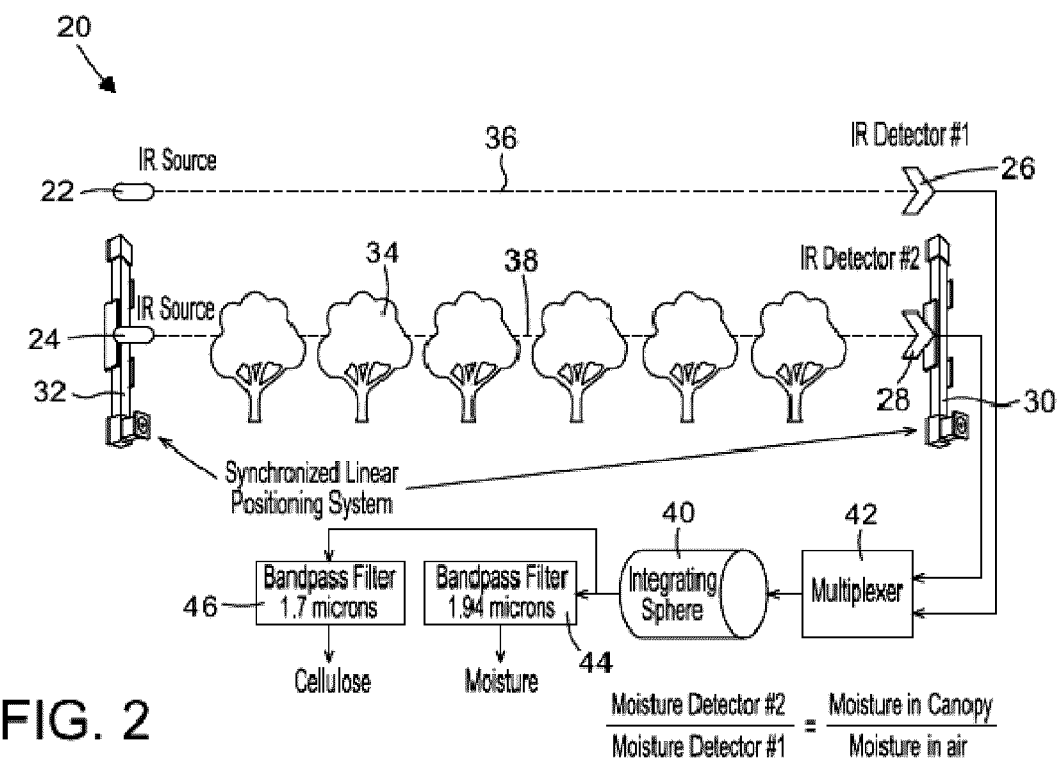
FIG. 2 shows schematically a canopy moisture content measurement system according to one example embodiment.

As illustrated in FIG. 2, the inventors have now developed a system 20 for measuring the moisture content in the plant canopy using a pair of infrared (IR) sources 22, 24 and detectors 26, 28. In some embodiments, infrared (IR) sources 22, 24 are generated by taking a beam of infrared radiation from a single infrared source and splitting the beam into two equal beams 22, 24.

A first or measuring IR source 24 passes infrared radiation through the plant canopy 34 at a desired elevation along a path of travel 38 to provide a sample measurement (i.e. a measured IR parameter) and the second or reference IR source 22 also emits infrared radiation that does not pass through the plant canopy 34 but instead passes instead through a path of travel 36 that extends only through the air to provide a reference measurement (i.e. a reference IR parameter). The length of path of travel 36 is approximately the same as the length of path of travel 38.

The first or measuring IR source 24 that passes through the plant canopy and its associated first or measuring detector 28 are capable of being precisely aligned, for example using a pair of corresponding vertical actuators 30, 32 adapted to adjust the vertical position of measuring IR source 24 and measuring detector 28. Vertical actuators 30, 32 are an example of a synchronized linear positioning system for IR measuring source 24 and measuring detector 28, and any suitable synchronized linear positioning system that allows alignment of measuring IR source 24 with measuring detector 28 could be used.

In some embodiments, vertical actuators 30, 32 also allow measuring IR source 24 and measuring detector 28 to be moved together vertically as the plant grows, so that the measurement of infrared radiation transmitted by the plant canopy 34 is taken at a path of travel at desired elevation 38 that may move as the plants grow. In some embodiments, vertical actuators 30, 32 allow measuring IR source 24 and its corresponding measuring detector 28 to be moved up and down to measure IR transmission at different elevations within the plant canopy 34, e.g. to allow an average canopy moisture to be determined for a given group of one or more plants that together form the plant canopy 34. In some embodiments, vertical actuators 30, 32 allow the use of only one IR source and one IR detector, rather than two as illustrated in FIG. 2, as the single IR source and single IR detector can be actuated vertically between path of travel 38 through the plant canopy and path of travel 36 through the air, to measure both IR transmission through the plant canopy to provide a sample measurement value and IR transmission through the air to provide a reference value.

The reference IR source 22 and reference detector 26 that measure IR along a path 36 that does not pass through the plant canopy can be used as a reference value for the moisture content in the air (humidity) by measuring the infrared radiation absorbed by the air along path of travel 36, and compared to sample values obtained by the measuring IR source 24 and measuring detector 28 that pass though the plant leaves in the canopy as well as air along path of travel 38. The difference between the signal received at each detector 26, 28 can be used to infer the moisture content present in the leaves of the plant canopy, or other properties that can be assessed using infrared spectroscopy, as described below. That is, sample data obtained by the one beam of infrared radiation that passes through the plant canopy 34 along path of travel 38 is compared to the reference data for the other beam of infrared radiation that does not pass through the canopy but only along path of travel 36 through the air to obtain information about the level of moisture in the plant canopy 34, the level of biomass or cellulose in the plant canopy 34, and/or the level of plant stress being experienced by the plants that make up the plant canopy 34, as reflected by the IR absorbance of various indicators including abscisic acid (ABA), potassium, nitrogen, phosphorus, cellulose, biomass, chlorophyll and the like.

While in the illustrated embodiment, first and second IR sources 22, 24 and first and second detectors 26, 28 have been illustrated as being provided to measure a reference IR transmission and a measured sample IR transmission, respectively, in some embodiments, a single IR source and a single IR detector could be provided. The single IR source and single IR detector could be moved vertically, for example along vertical actuators 30, 32, to allow a first measurement of infrared radiation transmission at a vertical point that is outside of the plant canopy along path of travel 36 to provide a reference IR transmission value, and moved to allow a second measurement of infrared radiation at a vertical point such that the infrared radiation passes through the plant canopy at the desired measurement location along path of travel 38 to provide a measured sample IR transmission value.

In some embodiments, rather than measuring the reference IR transmission value through a path of travel 36, a reference IR transmission value is set in some other manner, for example by measuring the IR transmission of a portion of a dried plant (e.g. a dried leaf or leaves) or an entire dried plant, to provide the reference IR transmission value, or by measuring the IR transmission value through the plant canopy at a control wavelength at which the spectral properties of the material of interest are different from the spectral properties of the material at the measuring wavelength that is used to obtain the measured sample value. For example, in some embodiments in which the material of interest to assess plant health is water, the measured sample value is obtained by measuring IR transmission at a wavelength or band of wavelengths in the region of 1940 nm, including e.g. 1900, 1910, 1920, 1930, 1950, 1960, 1970 or 1980 nm, while the reference sample value is obtained by measuring IR transmission at a wavelength or band of wavelengths in the region of 1700 nm, including e.g. 1660, 1670, 1680, 1690, 1710, 1720, 1730 or 1740 nm.

It will be apparent to those skilled in the art that the measured IR can be passed through an optical band-pass filter to pass a range of wavelengths, and the power at a band sensitive to the element of interest (i.e. at which the element of interest exhibits significant changes in the measured IR property with changes in its concentration or changes in plant health) can be measured and compared to another band that is not sensitive (or is less sensitive) to the element of interest. Thus, in some embodiments, a band centred at a first wavelength that is highly sensitive to the element of interest is compared to a reference band centred at a second wavelength that is not sensitive to or has only a limited degree of sensitivity for the element of interest (e.g. a wavelength at which the element of interest does not have any or has minimal absorption). In one example embodiment, a second wavelength that has a limited degree of sensitivity for the element of interest is one at which a measured IR parameter for an element of interest has a maximum reading that is less than about 20%, less than about 15%, less than about 10% or less than about 5% of a maximum reading for the element of interest at the first wavelength that is highly sensitive to the element of interest. In another example embodiment, a second wavelength that is not sensitive to the element of interest has a maximum reading that is less than about 2%, less than about 1% or less than about 0.5% of a maximum reading for the element of interest at the first wavelength that is highly sensitive to the element of interest. Thus as an example, in some embodiments in which the element of interest is water, a band in the range of about 1900-1990 nm could be compared against a band in the range of about 1660-1740 nm to evaluate the presence of water, because the absorbance of IR by water in the 1900-1990 nm band is relatively high (i.e. this band is highly sensitive to water as the element of interest), while the absorbance of IR in by water in the 1660-1740 nm band is very low (i.e. this band is not sensitive to water as the element of interest.

In still further alternative embodiments, rather than measuring the infrared radiation that is transmitted through the plant canopy along path of travel 38, detectors 26 and 28 could be configured to measure the amount of infrared radiation that is reflected by (a) the ambient air to provide a reference IR reflectance value and (b) the plant canopy to provide a measured IR reflectance value, so that the reflection of infrared radiation by the plant canopy 34 could be used to obtain information about the level of moisture in the plant canopy 34, the level of biomass or cellulose in the plant canopy 34, and/or the level of plant stress being experienced by the plants that make up the plant canopy 34. In some embodiments, rather than using the reflectance of ambient air to provide a reference IR reflectance value, the reference IR reflectance value is obtained using a dried plant or a portion of a dried plant (e.g. a dried leaf or leaves, or an entire dried plant) to provide the reference IR reflectance value. In still other embodiments, the reference IR reflectance value is obtained by measuring the IR reflectance value at a control wavelength at which the spectral properties of the material of interest are different from the spectral properties of the material at the measuring wavelength that is used to obtain the measured sample value. For example, in some embodiments in which the material of interest to assess plant health is water, the measured sample value is obtained by measuring IR reflectance at a wavelength or band of wavelengths centred in the region of 1940 nm, including e.g. 1900, 1910, 1920, 1930, 1950, 1960, 1970 or 1980 nm, while the reference sample value is obtained by measuring IR transmission at a wavelength or band of wavelengths in the region of 1700 nm, including e.g. 1660, 1670, 1680, 1690, 1710, 1720, 1730 or 1740 nm.

Any suitable means of processing the optical data obtained by detectors 26, 28 can be used in various embodiments. In the illustrated embodiment, by collecting energy from each detector using an integrating sphere 40, optionally after passing the received signals through a multiplexer 42, the received energy at each detector can be presented to optical band-pass filters 44, 46 that isolate the energy in different bands of wavelength. For example in one example embodiment where the material of interest to monitor plant health is water, as it is known that water attenuates wavelengths centered at 1.94 microns (1940 nm), by looking at the energy in a narrow band centered at 1.94 microns, the amount of moisture in the air can be determined from the IR received by reference detector 26, and the amount of moisture in the air plus the leaves in plant canopy 34 can be determined from the IR received by measuring detector 28.

In some such example embodiments, a band that is not sensitive to moisture, e.g. centered at 1.7 microns (1700 nm), can further be examined and used as a reference value to calculate the difference between the reference IR beam that passes only through air along path of travel 36 and the measured IR beam at 1.94 microns (1940 nm) that passes through the plant canopy along path of travel 38, and this difference can be used to calculate the amount of plant biomass or cellulose that is present in the canopy. In some embodiments, the reference measurement is obtained by measuring the band that is not sensitive to moisture centered at 1.7 microns (1700 nm) through the plant canopy along path of travel 38, and this value is used as the reference value and compared to the measured value determined by using the measured IR beam at 1.94 microns (1940 nm) that passes through the plant canopy along path of travel 38 to determine how much water is in the plant canopy and evaluate plant health.

In some embodiments, the wavelength of infrared radiation that is used is in the range of about 0.5 to about 3 microns, including any value therebetween e.g. 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8 or 2.9 microns. In some embodiments, the wavelength of infrared radiation that is used is in the range of about 0.5 to 10 microns, including any value therebetween e.g. 0.75, 1.0, 1.25, 1.50, 1.75, 2.0, 2.5, 3.0, 3.5, 4.0, 4.5, 5.0, 5.5. 6.0, 6.5, 7.0, 7.5, 8.0, 8.5, 9.0 or 9.5 microns.

In some embodiments, IR sources 22, 24 are broad-spectrum IR sources. In some embodiments, IR sources 22, 24 comprise a single broadband source split into two paths. In some embodiments, IR sources 22, 24 are a coherent source, e.g. a laser, with a given spectral response.

Abiotic stress is the most harmful factor concerning the growth and productivity of plants. When a plant experiences a drought condition, the pores in the shape of mouths (stomata) that are found in the epidermis on the underside of a leaf close to prevent further water loss. This leads to a reduction of $CO_2$ gas exchange and hence reduces the productivity of photosynthesis according to Equation (2):

$$6H_2O + 6CO_2 \rightarrow C_6H_{12}O_6 + 6O_2 \qquad (2)$$

During early onset of drought conditions, abscisic acid (ABA) stress hormones originating from the roots are transported in the xylem and delivered to the leaves. The ABA levels are increased in the leaves to trigger stomatal closure. When this closure signal occurs the stomata guard cells lose potassium ions ($K^+$) which results in water diffusing out of the cells; as this occurs, the guard cells become flaccid and less bowed, which closes the stomata. Thus, the level of ABA and/or the level of potassium ions in the plant canopy can be measured and used as an indicator of plant stress levels. It is expected that levels of potassium and nitrogen would decrease after an increase in the level of ABA. Likewise, a decreasing level of water present in the plants, a decreasing level of cellulose material or biomass present in the plants, or a decrease of chlorophyll in the plants can all be indicators of plant stress, and can be monitored accordingly and used to regulate the delivery of resources such as water, humidity, light, carbon dioxide and/or nutrients to the plants to help to optimize plant health while minimizing the waste of such resources by avoiding a need to deliver an excess of such resources.

In one embodiment, a method of measuring the levels of materials of interest as a plant health parameter to monitor plant health such as water, biomass, cellulose, chlorophyll, ABA, potassium, phosphorus, nitrogen and the like in a leaf, plant or plant canopy is taught herein using infrared (IR) wavelengths compared between frequencies which are sensitive to the plant health parameter under stress conditions, but not sensitive to the underlying properties of the plant biomass. Therefore, in addition to or as an alternative to measuring the amount of water content in the leaf and/or biomass or cellulose contained in the plant canopy, abiotic stress level conditions can be quantified from the initial onset of stress, to total crop loss; where total crop loss is defined at the permanent wilting point (PWP), which is where the soil moisture has diminished beyond the point that the plant can recover from drought (i.e. beyond the permanent wilting point, the plant cannot recover from drought stress). The permanent wilting point (PWP) corresponds to the inferior limit of available water. This moisture condition severely restricts the absorption of water by the plants, which will die if there is no replacement of the water in the soil. In general, the permanent wilting point is also determined in the laboratory, by the retention curve method. The permanent wilting point may vary as between different plants, but in some embodiments is on the order of e.g. approximately −1.5 MPa. In some cases plants may have a permanent wilting point down to as low as −6 MPa.

Figure 3:
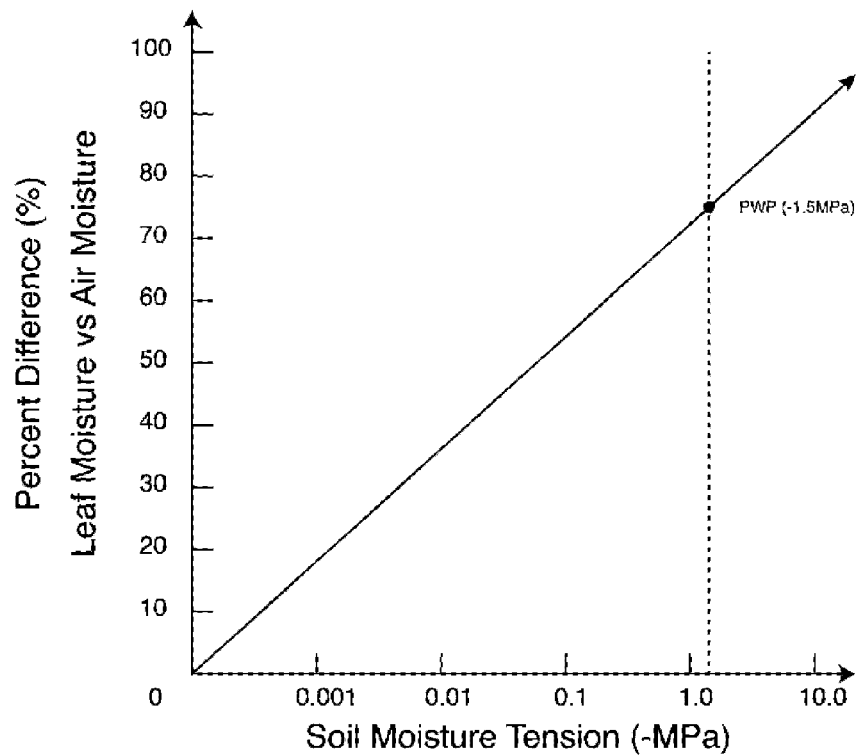
FIG. 3 shows the percent difference (%) between leaf moisture content vs. air moisture content with increasing soil moisture tension (the force per unit area required to move water in the soil, which is reflective of how dry the soil is). As the difference between leaf moisture content and air moisture content increases, the plant becomes more stressed up to the permanent wilting point (PWP).

FIG. 3 shows the percentage difference between the moisture content in the leaf versus the moisture content in the air as soil moisture tension decreases. The percent difference will increase as the plant transpiration rate increases from a well-watered condition, up to the initial on-set of stress; this region is defined as the optimum irrigation range. Beyond the optimized irrigation range the percent difference will continue to increase as the plant becomes more stressed up to total crop lost: permanent wilting point (PWP).

Figure 4:
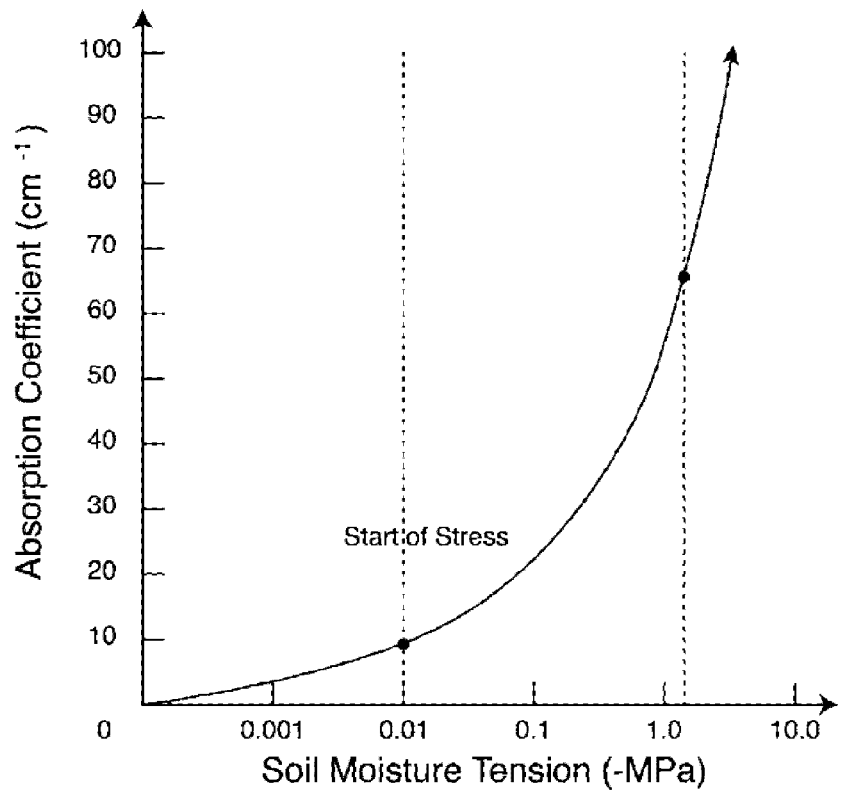
FIG. 4 shows the hypothetical increase in absorption of infrared radiation due to increase in stress hormone abscisic acid (ABA) in the leaf, and a decrease of $K^+$ in the guard cells with increasing soil moisture tension.

The end point of the optimum irrigation range is defined at the point where ABA levels are initially detected. FIG. 4 shows a hypothetical increase in the absorption coefficient due to the increase in stress hormone abscisic acid (ABA) levels in the leaf with increasing soil moisture tension, which results in stomatal closure from potassium ions being pumped out of the stomata guard cells. In some embodiments, the absorption coefficient used to evaluate the level of abscisic acid (ABA) in the plant canopy is measured at a wavelength or band of wavelengths centred at approximately 5800-6250 nm (including any value therebetween, e.g. 5850, 5900, 5950, 6000, 6050, 6100, 6150 or 6200 nm) as the wavelength that is highly sensitive to abscisic acid as the element of interest.

Figure 5:
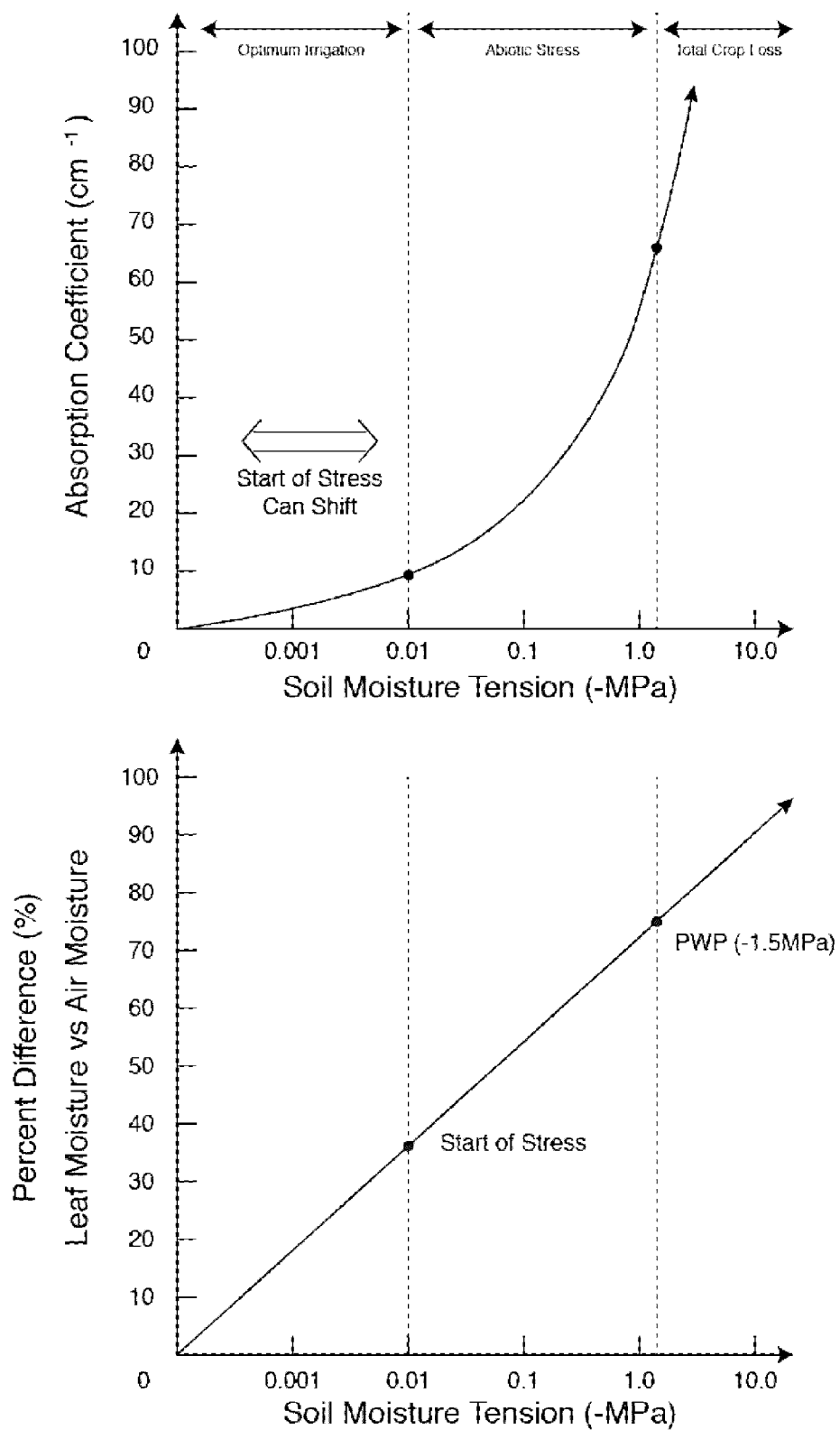
FIG. 5 shows the relationship between leaf moisture content deficit (lower panel) and the rate of stress, as confirmed by the hypothetical increase in absorption of infrared radiation at wavelengths sensitive to a plant health parameter reflective of stress, e.g. abscisic acid (upper panel). Also shown are the optimum irrigation range, stress range (abiotic stress or start of stress) and total crop loss conditions relative to increasing soil moisture tension.

FIG. 5 combines FIGS. 3 and 4 to show how the indication of an increase in hypothetical absorption signal from ABA levels during water deficit can indicate the early onset of plant water stress. More importantly, this information can be used by a control system to control the water transpiration rate (e.g. by regulating the supply of water to the plant and/or soil), and also the amount of abiotic stress to steer the plant to be vegetative (production of leaves and stem), or force a generative state (production of flowers, fruit and seeds). For example, once the absorption coefficient of abscisic acid reaches a predetermined level, an irrigation system may be activated to supply water to the plants. The initial on-set of stress may also shift depending on crop variety and development stages, meaning that the predetermined level of abscisic acid that triggers activation of the irrigation system may be adjusted depending on the particular crop and conditions at any given time and location.

Since many greenhouses and grow rooms have multiple rows of plants as well as tiers of plants, in some embodiments the IR source and detector that measure the plant canopy are mounted on a linear actuator to move back and forth along the x-axis (i.e. horizontally) to measure multiple rows of plants. A linear actuator moving along a y-axis (i.e. vertically) would allow the source and detector to be positioned to measure multiple tiers of plants in grow rooms.

Figure 6:
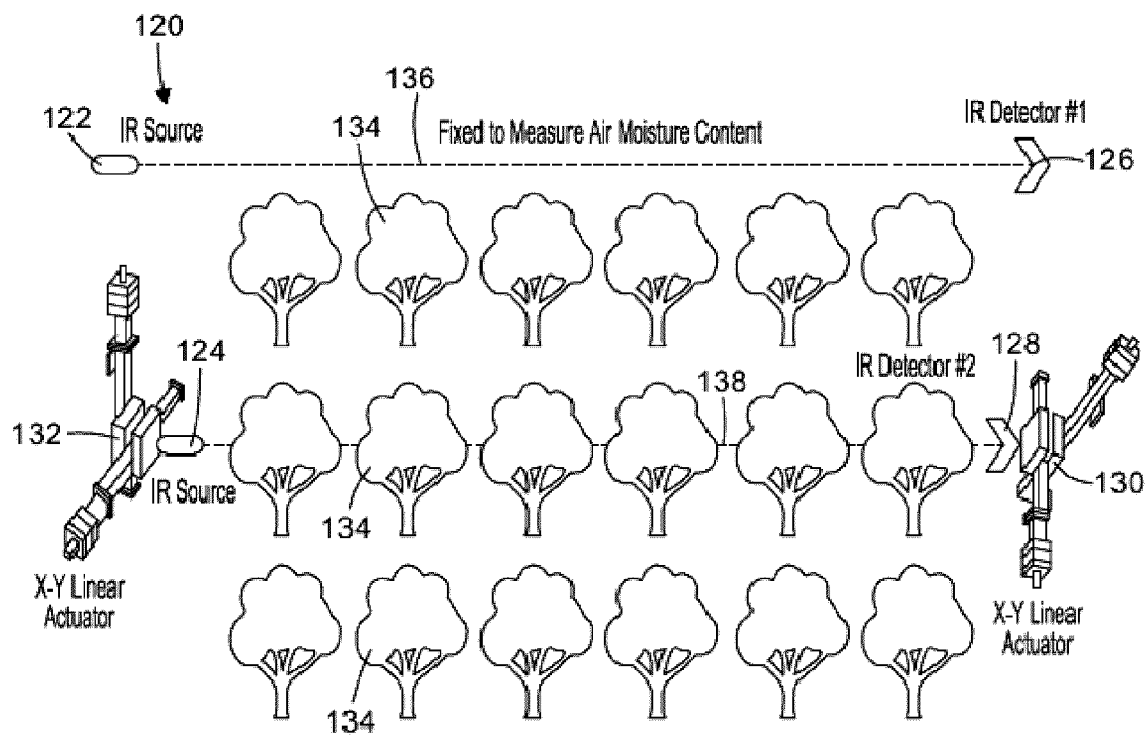
FIG. 6 shows schematically an example embodiment of a movable IR source and detector configured to measure the canopy moisture content and/or plant health of multiple tiers of plants.

An example embodiment of a system 120 for use to measure infrared radiation transmission through a plurality of different rows and tiers of plants is illustrated in FIG. 6. The components of system 120 are generally similar to the components of system 20, and like elements have been illustrated with like reference numerals incremented by 100.

System 120 differs from system 20 in that the measuring IR source and the measuring IR detector can be moved both horizontally, to measure IR transmission through a plurality of different rows of plants, and vertically, to measure IR transmission through a plurality of different tiers of plants and/or at different elevations within the canopy 138 of the same row of plants.

In the illustrated embodiment, the X-Y linear actuator shown is a motor-driven screw drive 130, 132. In some embodiments, the X-Y linear actuator is belt driven to move over several meters in both the X- and Y-directions. Any suitable mechanism and apparatus can be used to facilitate motion of components of system 120 in both the X- and Y-directions.

The percent moisture in the canopy can be determined from the following calculation in Equation (3) based on the amount of moisture determined by the measuring detector (i.e. the sample measurement) and the reference detector (i.e. the reference measurement):

$$\% \text{ Moisture}_{(Plant\ Canopy)} = 100 * \frac{(\text{Moisture}_{(Meas\ Det)} - \text{Moisture}_{(Ref\ Det)})}{\text{Moisture}_{(Ref\ Det)}} \quad (3)$$

Equation (3) can be used to calculate the percentage of moisture present in the plant canopy relative to a fully hydrated plant canopy based on a measured IR parameter of the plant canopy relative to a reference IR parameter. In some example embodiments, the percentage of moisture present for a particular measured IR parameter is determined empirically by calculating a calibration curve by measuring the value of the IR parameter for a particular plant canopy 34 or sample of the plant canopy 34 (e.g. a leaf) at a plurality of different known percentage moisture contents.

The percent plant biomass or cellulose can be calculated based on the intensity of the transmitted infrared radiation as follows from Equation (4) based on the amount of biomass determined by the measuring detector and the reference detector:

$$\% \text{ Biomass} = 100 * \frac{(\text{Biomass}_{(Measuring\ Detector)} - \text{Biomass}_{(Reference\ Detector)})}{\text{Biomass}_{(Reference\ Detector)}} \quad (4)$$

In some embodiments, biomass is determined by measuring spectral properties of the sample at a wavelength or band of wavelengths centred in the range of between about 800 and 1300 nm, including any value therebetween, e.g. 850, 900, 950, 1000, 1050, 1100, 1150, 1200 or 1250 nm.

In some embodiments, Equation (4) can be used to calculate the amount of plant material, biomass or cellulose between the source and detector as a measure of plant yield. In some example embodiments, the biomass value for a particular measurement of transmitted infrared radiation is determined empirically by calculating a calibration curve by measuring the value of transmitted infrared radiation for a particular plant canopy 34, and then drying and measuring the weight of that particular plant canopy 34 to determine the amount of biomass present in that particular plant canopy 34.

In some embodiments, rather than measuring the transmission or reflectance of infrared radiation through or by a plant canopy comprised of a plurality of plants, the IR source and IR detector are used to measure the transmission or reflectance of infrared radiation through or by a single plant or plant part (e.g. leaf) relative to ambient air. In some embodiments, such a method is conducted as described above, except that the path of travel through the plant canopy 38 extends only through a single plant or plant part (e.g. leaf). In other such embodiments, a reference IR source 22 and reference IR detector 26 are used to determine the IR absorption or transmission by ambient air or as compared with a control sample such as a dried portion of a plant (e.g. a dried leaf or leaves, or an entire dried plant), while a measuring IR source 24 and measuring IR detector 28 are used to measure the IR transmission through or IR reflectance from a single plant from the growing plant canopy. E.g. in embodiments in which IR transmission is measured, measuring IR source 24 is placed on a first side of the single plant to be assessed and measuring IR detector 28 is placed on a second side of the single plant to be assessed opposite the first side. The IR transmission measured by measuring IR detector 28 is then compared against a reference value for the IR transmission by an equivalent length segment of ambient air, or a control sample such as a dried plant or plant part such as a leaf, as measured by reference IR source 22 and reference IR detector 26 to measure the moisture content, biomass or cellulose content, and/or level of stress of the single plant.

In some such embodiments, measuring IR source 24 is the same as reference IR source 22 and measuring IR detector 28 is the same as reference IR detector 26, and a reference level of IR transmission or reflectance by ambient air is determined by measuring IR transmission or reflectance using measuring IR source 24 and measuring IR detector 28 to measure IR transmission or reflectance through or by a portion of ambient air having dimensions equivalent to the dimensions across which the IR transmission or reflectance by the single plant is measured.

In some embodiments, rather than relying on the IR transmission or IR reflectance as the IR parameter, a different IR parameter such as the absorbance or absorption coefficient is used as the IR parameter to evaluate the difference between the measured and the reference properties to monitor plant health.

In some embodiments, a control system to control the canopy transpiration—i.e. the passage of water through a plant from the roots, through the vascular system to the atmosphere—or canopy transpiration rate is provided.

Figure 7A:
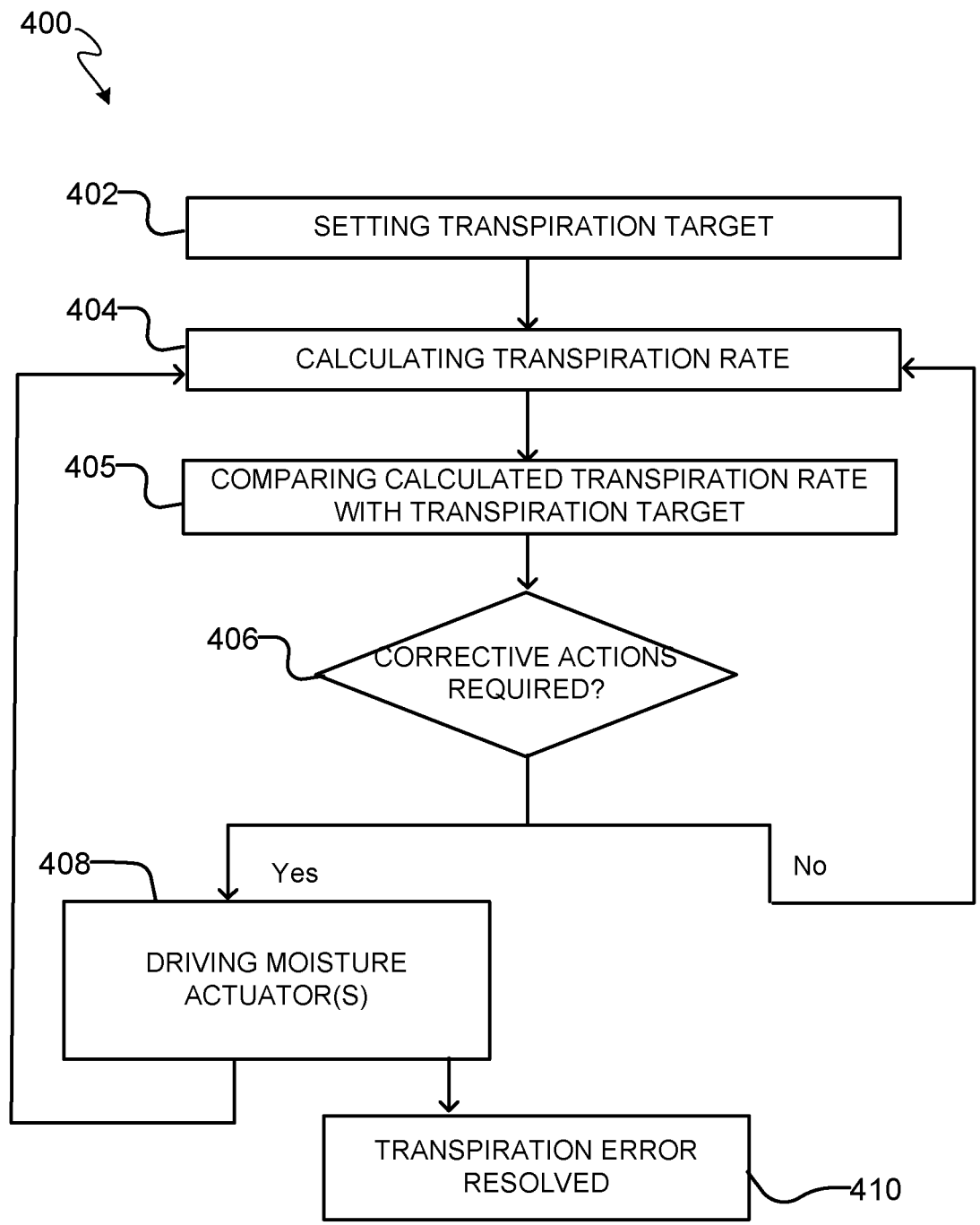
FIG. 7A shows a method for monitoring and adjusting plant canopy moisture to regulate plant transpiration.

In FIG. 7A, an example embodiment of a method 400 for monitoring and adjusting canopy moisture is shown. Method 400 may be implemented by a control system that has a transpiration rate target that changes with the plant cycle (illumination, temperature, etc.). At step 402, a transpiration target is set. At step 404, a calculated transpiration rate is obtained using the moisture measurement of the plant canopy by measuring transmitted or reflected infrared radiation of the plant canopy as herein disclosed, e.g. using an apparatus such as system 20 or 120. The transpiration rate of plants can be modeled based on environmental data collected from the environment surrounding the plant and the amount of water and nutrients supplied to the plants. Without being bound, measuring the moisture present in the leaves of the plants, for example using the methods described herein involving measurement of an IR parameter, removes one of the modeled sources of error from traditional methods of calculating transpiration rates, and is expected to improve the accuracy with which transpiration rate can be modeled.

At step 405, the transpiration target is compared to the calculated transpiration rate. If the transpiration target differs from the calculated transpiration rate, a transpiration error is generated at step 406 and is fed into an appropriate controller (in this example, a proportional-integral-derivative controller or PID) which then at step 408 drives the moisture actuators watering the plants until such time as the transpiration error is driven to zero (at step 410).

Figure 7B:
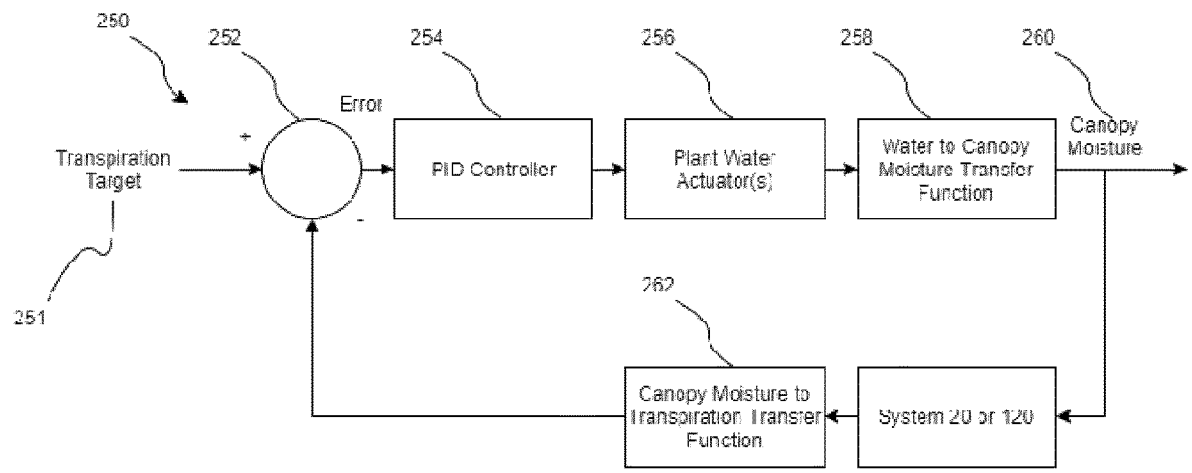
FIG. 7B shows an example embodiment of an apparatus that can be used to carry out such a method.

In FIG. 7B, an example embodiment of an apparatus 250 that can be used to carry out method 400 or method 400' is shown. At 252 a processor determines there is a transpiration error such as an increase or decrease in the level of moisture in the plant canopy (e.g. as caused by the presence of an excess or a deficit of water in the soil). A PID controller 254 can be used to drive plant water actuators 256. A water-to-canopy moisture transfer function executed by a processor 258 can be used to determine an expected amount of moisture that should be driven to the plant canopy 260. A suitable system, such as system 20 or system 120 described above, can be used to evaluate the level of moisture in the plant canopy, and the result of that assessment can be supplied to a canopy moisture to transpiration transfer function executed by a processor 262, which feeds back to 252 to allow for a determination of whether additional moisture should be supplied to the canopy (i.e. that a transpiration error still persists to be addressed).

Figure 8:
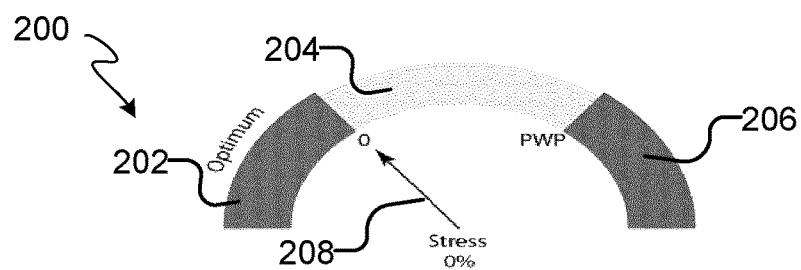
FIG. 8 shows an example embodiment of a stress gauge provided for use with a software interface for providing an operator with a visual indication of a stress level of a crop.

In some embodiments, a software interface is used to provide an operator with a visible, audible or other perceptible indication of the stress level of the crop. As shown in FIG. 8, in one example embodiment, a stress gauge 200 is provided to provide a visible indication to an operator of the stress level of the crop. The stress gauge has regions for indicating where plants are experiencing optimum conditions (202), where plants are beginning to experience stress through to the permanent wilting point (PWP) (204), and where plants have gone past the permanent wilting point (PWP) (206). An indicator 208 provides the operator with a visible indication of the stress level of the crop. In alternative embodiments or in conjunction with such a gauge, the system could provide an audible indication such as a beep, tone, alarm or the like, and/or an alternative or additional visual indication such as a flashing warning light, to alert an operator to the fact that the crop is experiencing or approaching a stress condition.

In some embodiments, a control system is provided to control the supply of resources such as water, humidity, light, carbon dioxide, nutrients and so on to a crop for optimum performance and cost savings. It is often desired to maximize photosynthesis (Equation (2), i.e. $6H_2O+6CO_2 \rightarrow C_6H_{12}O_6+6O_2$). To achieve this, water, humidity, carbon dioxide and/or light energy must be available. However, supplying an overabundance of resources such as water, humidity, carbon dioxide and/or light decreases efficiency and increases cost. It is therefore desirable to supply only the level of resources needed to maintain optimum crop conditions, to minimize costs and waste.

Figure 9A:
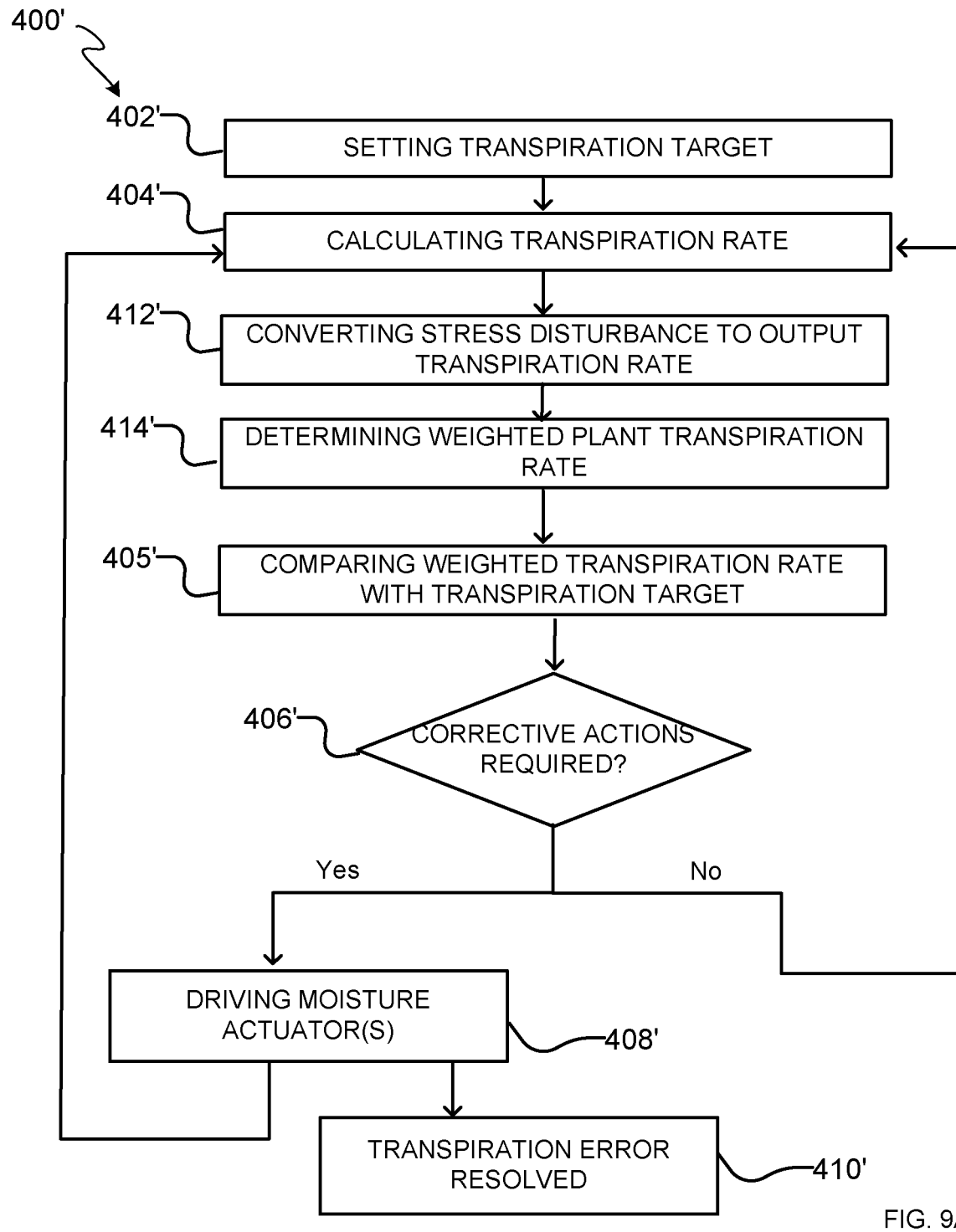
FIG. 9A shows the effect of additional stress disturbance in an example embodiment of a method for monitoring and adjusting plant canopy moisture.

FIG. 9A shows an example embodiment of a method 400' for monitoring and adjusting canopy moisture as a way to optimize the supply of the resource water to the crop. Method 400' is similar to method 400 and similar steps are shown with reference numerals marked with the prime symbol. Method 400' considers the addition of a stress disturbance into a target transpiration rate set for a controller. For example, if the transpiration rate is higher than the rate of water uptake from the root-zone, drought onset may occur; the control system would deliver water to the plant to reduce the stress metric to appropriate levels. A controller such as a proportional-integral-derivative (PID) controller regulates the adjustment of environmental conditions such as water, light, carbon dioxide levels, and so on to achieve this.

At step 412', a function G(s) converts the adjustment of the environmental conditions by PID controller into measured outputs, for example, plant transpiration rate, plant stress, and so on. At step 414', a weighted transpiration rate is determined where the effect of the stress disturbance on the calculated transpiration rate is addressed. For example, F(s), a feedback transfer function is used to convert the measured outputs from G(s) into the weighted plant transpiration rates, which can be compared to the setpoint and the stress disturbance presented to PID controller at step 405'. Necessary corrective action such as driving moisture actuators via the PID controller can be carried out at steps 406' and 408' until the transpiration error is resolved at 410'.

FIG. 9B shows an example embodiment of a system 360 that can be used, inter alia, to carry out method 400'. System 360 enables the addition of a stress disturbance 352 into a target transpiration rate set for a controller 350. If the transpiration rate is higher than the rate of water uptake from the root-zone, drought onset may occur; the control system would deliver water to the plant to reduce the stress metric to appropriate levels. The proportional-integral-derivative (PID) controller 350 regulates the adjustment of environmental conditions such as water, light, carbon dioxide levels, and so on to achieve this. A function G(s) executed by a processor 354 converts the adjustment of the environmental conditions by PID controller 350 into measured outputs, for example, plant transpiration rate, plant stress, and so on. A function F(s) executed by a processor 356 is a feedback transfer function that converts the measured outputs from G(s) 354 into plant transpiration rates, which can be compared to the setpoint and the stress disturbance 352 presented to PID controller 350 to adjust the environmental conditions as needed.

Subsequent to the above stress conditions, if the detected stress levels are not returned to appropriate levels (i.e., stress continues, or rate increases), since the stomata are closed there will be a reduction carbon dioxide gas exchange, and additional light energy (i.e., heat) would only increase the level of stress resulting for additional evapotranspiration (mainly from the root-zone). To prevent further plant damage, and/or save resource costs, the control system would turn off any supplemental carbon dioxide and/or supplemental lighting.

FIG. 10 shows an example embodiment of a method 500 for monitoring plant health. At 502, a measured sample IR parameter is measured. At 504, a reference IR parameter is measured. At 506, the control IR parameter is compared with the reference IR parameter to evaluate plant health at 508. For example, the measured sample IR parameter can be determined at a wavelength that is sensitive to changes in a plant health parameter, so that the measured sample IR parameter can be correlated to the state of health of the plant.

Any desired IR parameter that is sensitive to one or more plant health parameters at at least one wavelength can be used in various embodiments. In some embodiments, the IR parameter is IR transmission. In some embodiments, the IR parameter is IR reflectance. In some embodiments, the IR parameter is IR absorption. In some embodiments, the IR parameter absorption coefficient.

In some embodiments, the measured sample is a plant canopy, a single plant, or a plant leaf. In some embodiments, the reference IR parameter is determined by measuring the IR parameter across a path length that is equal to or approximately equal to the path length used to determine the measured sample IR parameter, but which does not contain any sample (i.e. which extends through ambient air only, with no plant canopy, plant or plant leaf disposed therein). In some embodiments, the reference IR parameter is determined by measuring the IR parameter for a control sample having known properties, for example a dried leaf, dried plant, or dried plant canopy, which is assumed to have a moisture content of 0%, or a fully hydrated leaf, fully hydrated plant, or fully hydrated plant canopy, which is assumed to have a 100% moisture content.

In some embodiments as illustrated in FIG. 11, a calibration curve is empirically determined for a given IR parameter with respect to a specific material of interest to be used to monitor plant health, so that the state of health of the plant can be determined at any desired time based on a measurement of the IR parameter. Those skilled in the art will be able to empirically determine a calibration curve depending on the particular IR parameter of interest and the selected control or reference value, and so method 600 that is illustrated is exemplary in nature only and is not limiting.

In method 600, at 602 the desired IR parameter is measured for a given sample (e.g. a plant or plant part (e.g. leaf) or plant canopy) in an unstressed state at a wavelength or band of wavelengths where the IR parameter is sensitive to changes in a plant health parameter. The sample is then subject to stress (for example by allowing the soil to begin to dry out so that the moisture content of the sample begins to decrease and/or indicators of stress such as abscisic acid are produced) at 604. The IR parameter is then measured at 606 with the sample in a slightly stressed state. This process of steps 604 and 606 are repeated at 608 for as many times as are required to take the plant to a fully stressed state (e.g. dried), or at least close enough to a fully stressed state that a representative calibration curve can be prepared at 610. At 612, based on the calibration curve obtained from the experimental data, a determination is made of how the desired plant health parameter (e.g. % moisture content or abscisic acid level) can be calculated from the measured IR parameter. For example, an equation may be derived to provide a quantitative measure to calculate the desired plant health parameter for any measured value of the measured IR parameter. For example, an equation may be derived to calculate the percentage moisture content of the plant by measuring the absorption coefficient of the plant at a wavelength or band of wavelengths centered at approximately 1940 nm.

Figure 12:
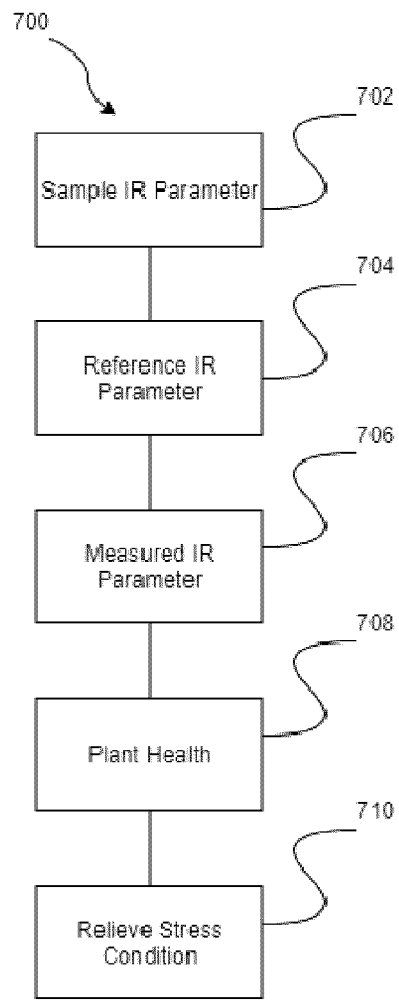
FIG. 12 shows an example embodiment of a method for controlling environmental parameters such as irrigation using a measured IR parameter.

With reference to FIG. 12, information as to the state of health of the plant derived from the measured IR parameter can then be used to make decisions and/or actuate equipment to shift the conditions of the plant towards a desired state of health. For example, with reference to method 700, the sample IR parameter can be determined at 702 and the reference IR parameter can be determined at 704. The sample IR parameter and the reference IR parameter can be compared to arrive at a measured IR parameter at 706. The measured IR parameter can be compared to the calibration curve and/or the equation derived from carrying out method 600 can be applied at 708 to determine the plant health condition parameter based on the measured IR parameter. If it is determined that the plant health condition parameter is indicative of stress, at 710, any advisable or desirable remedial action can be initiated, for example an irrigation system may be activated automatically to supply moisture to the plants if the stress condition is suggestive of a deficiency of water, or a visual or audible indicator may be activated so that a user of the system is alerted to the need to supply moisture to the plants.

For example, if the material of interest used to monitor plant health is the level of water in the plant canopy, then an IR parameter such as the absorption coefficient at approximately 1940 nm or a band of wavelengths centred at approximately 1940 nm can be used to determine the percentage moisture content in the plants. If the percentage moisture content is determined to be below a predetermined level that is considered acceptable based on the type of plant and the prevailing environmental conditions, then a decision can be made to supply water to the plants, optionally based on the activation of an audible or visual signal that water is needed, and/or an irrigation system can be automatically activated to supply water to the plants.

In alternative embodiments, other plant health parameters could be used in a similar manner by monitoring an appropriate IR parameter. For example:

The plant health parameter can be nitrogen, and the IR parameter can be evaluated at a wavelength or band of wavelengths centered at approximately 7.4 to 10 microns, including any value therebetween, e.g. 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8 or 9.9 microns.

The plant health parameter can be phosphorus, and the IR parameter can be evaluated at a wavelength or band of wavelengths centered at approximately 7000 to 8000 nm, including any value therebetween, e.g. 7050, 7100, 7150, 7200, 7250, 7300, 7350, 7400, 7450, 7500, 7550, 7600, 7650, 7700, 7750, 7800, 7850, 7900 or 7950 nm.

The plant health parameter can be potassium, and the IR parameter can be evaluated at a wavelength or band of wavelengths centered at approximately 2450 to 2470 nm, including any value therebetween, e.g. 2455, 2460 or 2465 nm.

The plant health parameter can be abscisic acid, and the IR parameter can be evaluated at a wavelength or band of wavelengths centered at approximately 5800 to 6250 nm, including any value therebetween, e.g. 5850, 5900, 5950, 6000, 6050, 6100, 6150 or 6200 nm.

The plant health parameter can be cellulose, and the IR parameter can be evaluated at a wavelength or band of wavelengths centred at approximately 800 to 1300 nm, including any value therebetween, e.g. 850, 900, 950, 1000, 1050, 1100, 1150, 1200 or 1250 nm.

The plant health parameter can be chlorophyll, and the IR parameter can be evaluated at a wavelength or band of wavelengths centred at approximately 400 to 800 nm, including any value therebetween, e.g. 420, 440, 460, 480, 500, 520, 540, 560, 580, 600, 620, 640, 660, 680, 700, 720, 740, 760 or 780 nm.

EXAMPLES

Certain embodiments are further described with reference to the following examples, which are intended to be illustrative and not limiting in nature.

Example 1.0—Determining Infrared Absorbance by Leaves Having Differing Moisture Contents Leaf samples were collected from three *Peperomia* plants. In particular, seven leaves were collected from each plant for drying. The weight of each leaf was measured, and the driest leaf was set as the control (i.e. provided the undried weight of the leaves).

One of the seven collected leaves was placed in a plastic bag and the remaining six were subsequently dried in an oven that was set to its warmest setting, at about 130° F. The six leaves were placed in the oven at the start of the experiment (t=0). After 1.5 hours, a first leaf was removed from the oven and placed in a plastic bag. The other five leaves were sequentially removed one at a time, after successive 30 minute periods, and were placed in plastic bags.

Figure 13A:
FIGS. 13A-13C show the appearance of undried and dried leaves in a verification experiment.
Figure 13A:
Figure 13A:
Figure 13A:
Figure 13A:
Figure 13A:
Figure 13A:
Figure 13B:
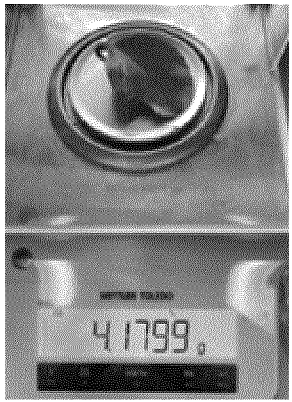
Figure 13B:
Figure 13B:
Figure 13B:
Figure 13B:
Figure 13B:
Figure 13B:
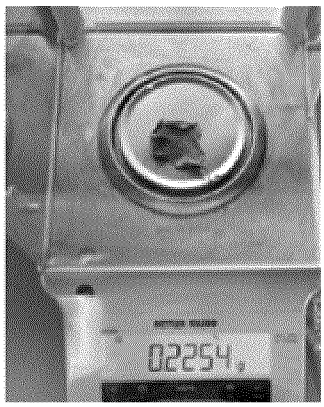
Figure 13C:
Figure 13C:
Figure 13C:
Figure 13C:
Figure 13C:
Figure 13C:
Figure 13C:

The weight of each of the undried leaf and the six dried leaves was determined using an analytical balance. The weight values are summarized in Table 1 below and the visual appearance of undried and dried leaves over the course of time is shown in FIGS. 13A, 13B and 13C along with the measured weight of each leaf. It can be seen that the leaves shrivel and decrease in size with increased drying time, as the level of moisture in the leaf is reduced.

TABLE 1

Experimentally determined weights of drying leaves.

|  | Fresh Leaf (t = 0) | First Leaf (t = 1.5 hours) | Second Leaf (t = 2.0 hours) | Third Leaf (t = 2.5 hours) | Fourth Leaf (t = 3.0 hours) | Fifth Leaf (t = 3.5 hours) | Control (Last Leaf) (t = 4.0 hours) |
|---|---|---|---|---|---|---|---|
| Trial 1 | 16971 g | 6840 g | 5337 g | 3113 g | 2247 g | 1164 g | 1115 g |
| Trial 2 | 41799 g | 13759 g | 8741 g | 8144 g | 6608 g | 2801 g | 2254 g |
| Trial 3 | 46754 g | 13387 g | 11970 g | 11252 g | 10840 g | 9745 g | 1779 g |

The IR transmission value of each of the undried and dried leaves was measured using an Agilent™ Cary 7000 Universal Measurement Spectrophotometer (UMS), which is capable of measuring both transmission (T) and reflectance (R). The software for the UMS was set up with the following criteria:

1. Spectrum range starts at 2500 nm and ends at 1100 nm
2. Reading to % transmittance (% T)
3. Check that there is zero/baseline setup
4. Enable UMA, to set the detector at a certain angle
   1. Set to 180 degrees
   2. Stationary Before measuring the IR transmission or reflectance value, the UMS was calibrated by setting a baseline for the instrument. The last leaf removed from the oven was used as the baseline in each trial. To set the baseline, the last leaf removed out from the oven was placed in the UMS and the baseline option was selected. Also, when prompted by the UMS, a black piece of material was placed in the UMS to set an IR transmission or reflectance value of zero.

Each leaf was placed at the center of the mount of the UMS. The orientation of each leaf was further adjusted to make sure that the laser would point directly at the center of the leaf (determined by a white light of the instrument that indicates the position of the laser). Once the leaf was fastened down and the laser was pointed at the center of the leaf, the lid of the UMS was closed and the IR transmission spectrum was obtained. Absorption coefficients were determined based on the measured transmission values. A peak in the absorption coefficient of the leaves was observed at a wavelength of approximately 1940 nm, consistent with the expected IR absorption peak of water.

To calculate the total water content of the fresh leaves prior to drying, the following Equation (5) was used:

$$\text{Total Water Content}_{Leaf} = \text{Fresh Leaf}(100\%) - \text{Control}_{(dried\ leaf)}(0\%) \quad (5)$$

To calculate the percentage water content of each leaf, the following Equation (6) was used:

$$\% \text{ Water Content of Leaf} = \frac{\text{Test Leaf} - \text{Control}_{(dried\ leaf)}(0\%)}{\text{Total Water Content of Leaf}} \times 100\% \quad (6)$$

The absorption coefficient was calculated using the following Equation (7), where T is the normal incidence transmission and l is the path length of the leaf through which the laser is passing, in cm:

$$\text{Absorption Coefficient (cm}^{-1}) = -\frac{\ln\left(\%\frac{T}{100}\right)}{l} \quad (7)$$

The calculated total water content is summarized in Table 2 below.

TABLE 2

Calculated total water content of fresh leaves.

| | Fresh Leaf |
|---|---|
| Trial 1 | (1.6971 g − 0.1115 g) = 1.5856 g |
| Trial 2 | (4.1799 g − 0.2254 g) = 3.9545 g |
| Trial 3 | (4.6754 g − 0.1779 g) = 4.4975 g |

The calculated percentage content of each leaf is summarized in Table 3 below.

TABLE 3

Percentage water content for each leaf.

| | Fresh Leaf | First Leaf | Second Leaf | Third Leaf | Fourth Leaf | Fifth Leaf | Control (Last Leaf) |
|---|---|---|---|---|---|---|---|
| Trial 1 | 100% | (0.6840 g − 0.1115 g)/ 1.5836 g = 36.1% | (0.5337 g − 0.1115 g)/ 1.5836 g = 26.7% | (0.3113 g − 0.1115 g)/ 1.5836 g = 12.6% | (0.2247 g − 0.1115 g)/ 1.5836 g = 7.15% | (0.1164 g − 0.1115 g)/ 1.5836 g = 0.31% | 0% |
| Trial 2 | 100% | (1.3759 g − 0.2254 g)/ 3.9545 g = 29.1% | (0.8741 g − 0.2254 g)/ 3.9545 g = 16.4% | (0.8144 g − 0.2254 g)/ 3.9545 g = 14.9% | (0.6608 g − 0.2254 g)/ 3.9545 g = 12.3% | (0.2801 g − 0.2254 g)/ 3.9545 g = 1.38% | 0% |
| Trial 3 | 100% | (1.3387 g − 0.1779 g)/ 4.4975 g = 25.8% | (1.1970 g − 0.1779 g)/ 4.4975 g = 22.7% | (1.1252 g − 0.1779 g)/ 4.4975 g = 21.1% | (1.0840 g − 0.1779 g)/ 4.4975 g = 20.1% | (0.9745 g − 0.1779 g)/ 4.4975 g = 17.7% | 0% |

The calculated absorption coefficients are summarized in Table 4 below.

TABLE 4

Calculated absorption coefficient for each leaf.

| | Wavelength (nm) | Leaf 1 (36.1%) Absorption Coefficient (cm$^{-1}$) | Leaf 2 (26.7%) Absorption Coefficient (cm$^{-1}$) | Leaf 3 (12.6%) Absorption Coefficient (cm$^{-1}$) | Leaf 4 (7.15%) Absorption Coefficient (cm$^{-1}$) | Leaf 5 (0.31%) Absorption Coefficient (cm$^{-1}$) |
|---|---|---|---|---|---|---|
| Trial 1 | 1940 | 35.33 | 20.70 | 9.19 | 13.29 | 1.80 |
| Trial 2 | 1940 | 51.23 | 26.72 | 22.06 | 13.65 | 2.17 |
| Trial 3 | 1940 | 55.00 | 28.05 | 24.28 | 20.88 | 18.81 |

Figure 14:
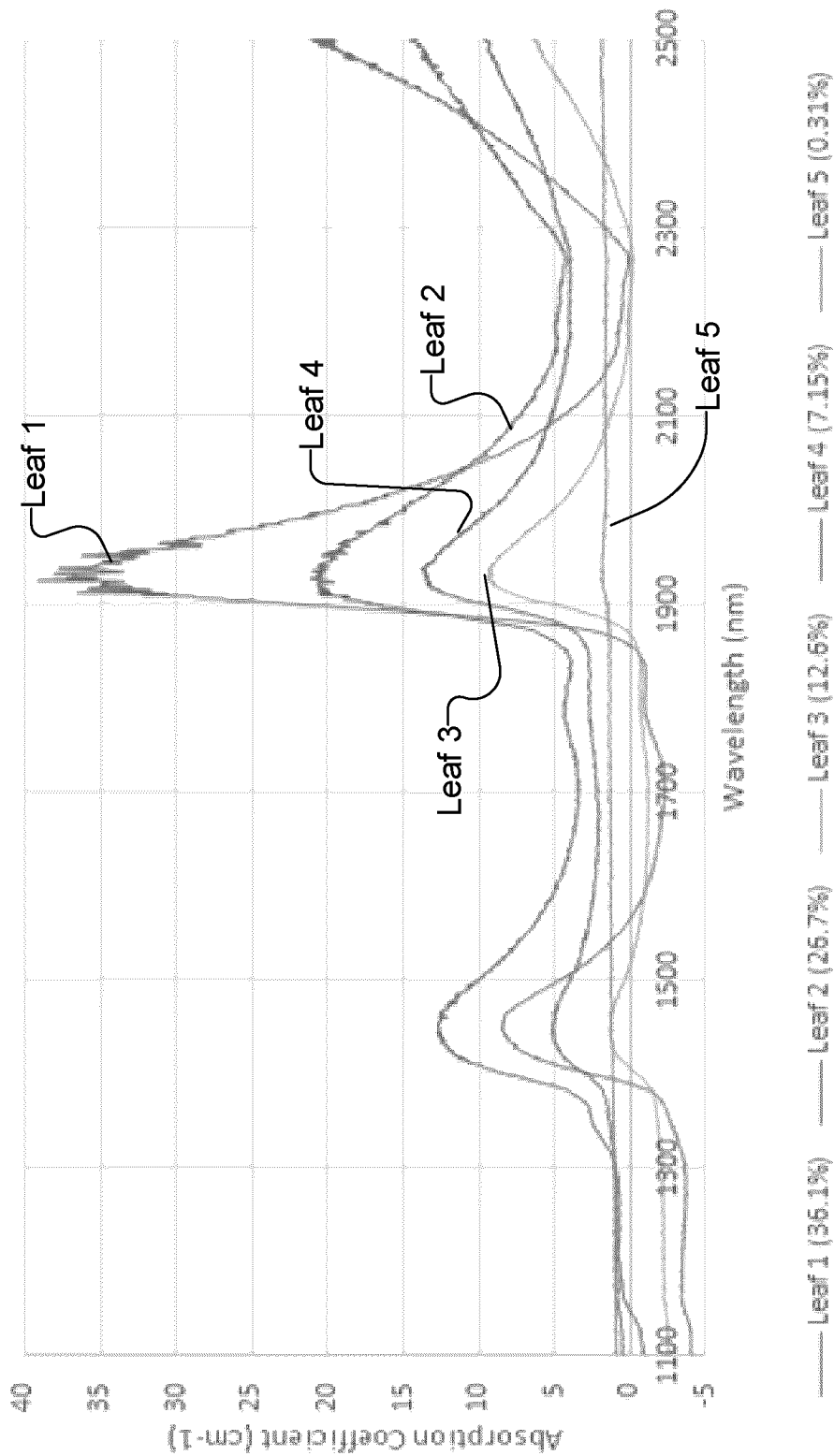
FIGS. 14-16 show absorption coefficient graphs versus wavelength obtained from the verification experiment referred to in FIGS. 13A-13C.
Figure 15:
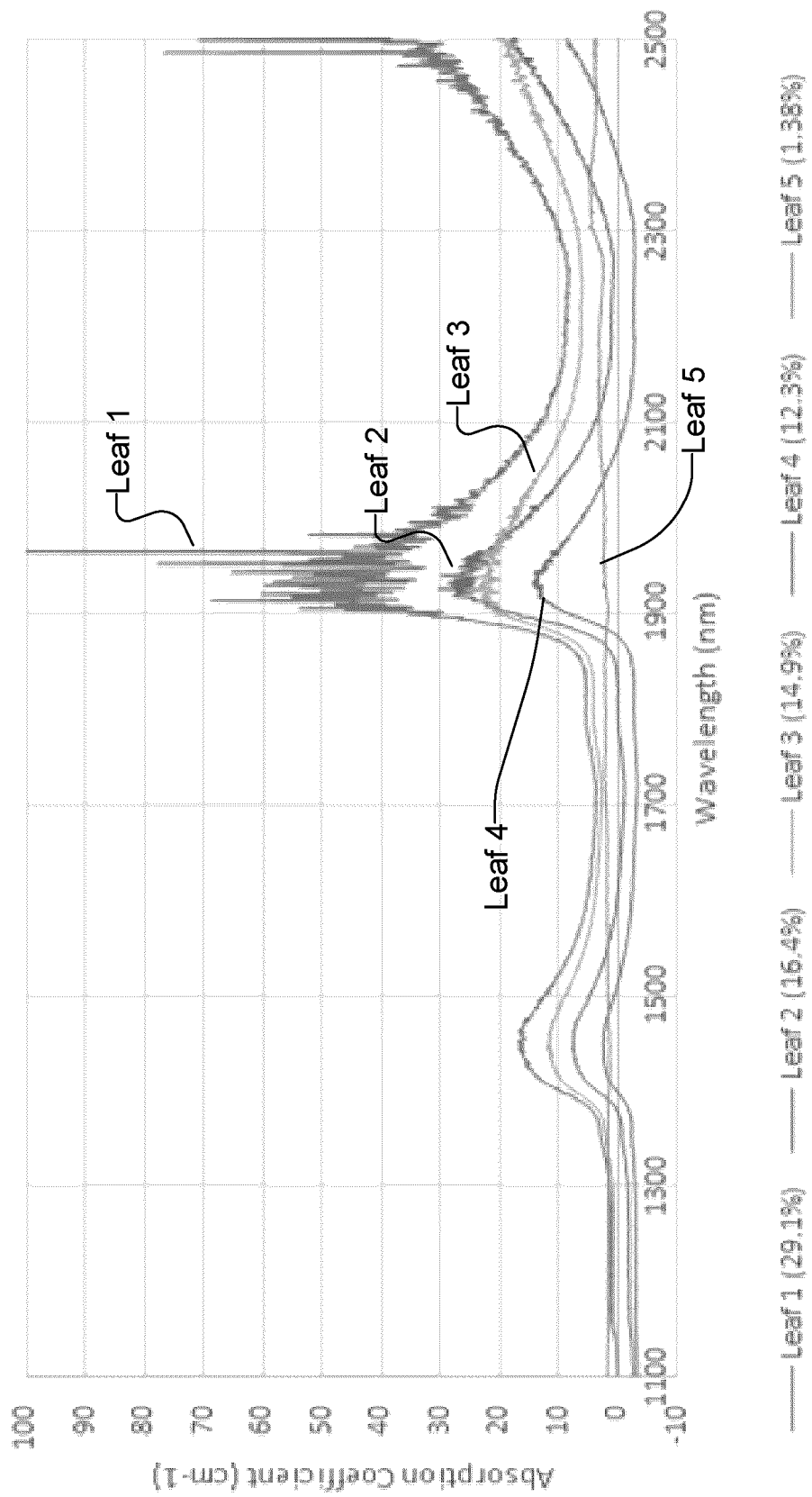
Figure 16:
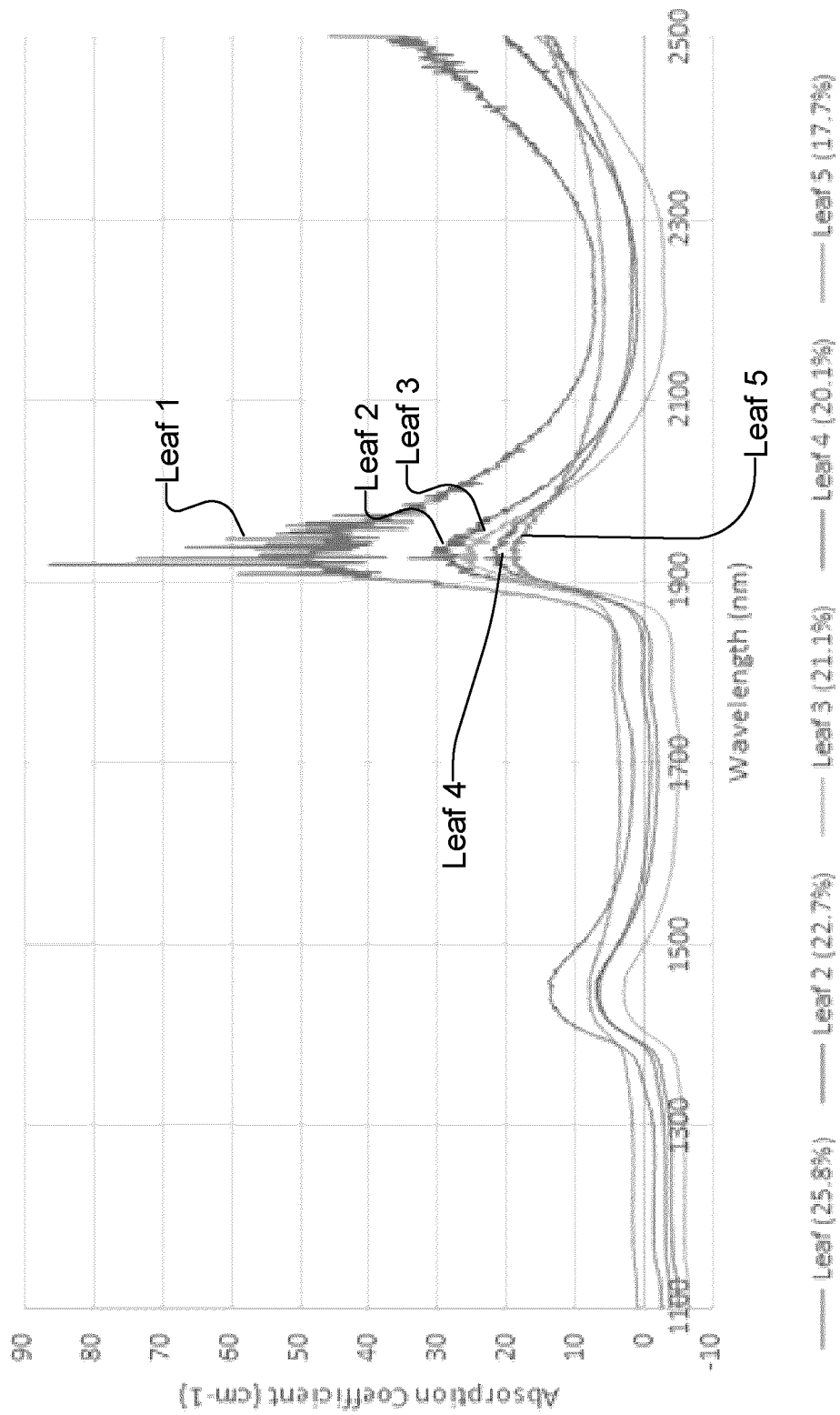

Absorption coefficient graphs for each of Trials 1, 2 and 3 are shown in FIGS. 14, 15 and 16.

Figure 17:
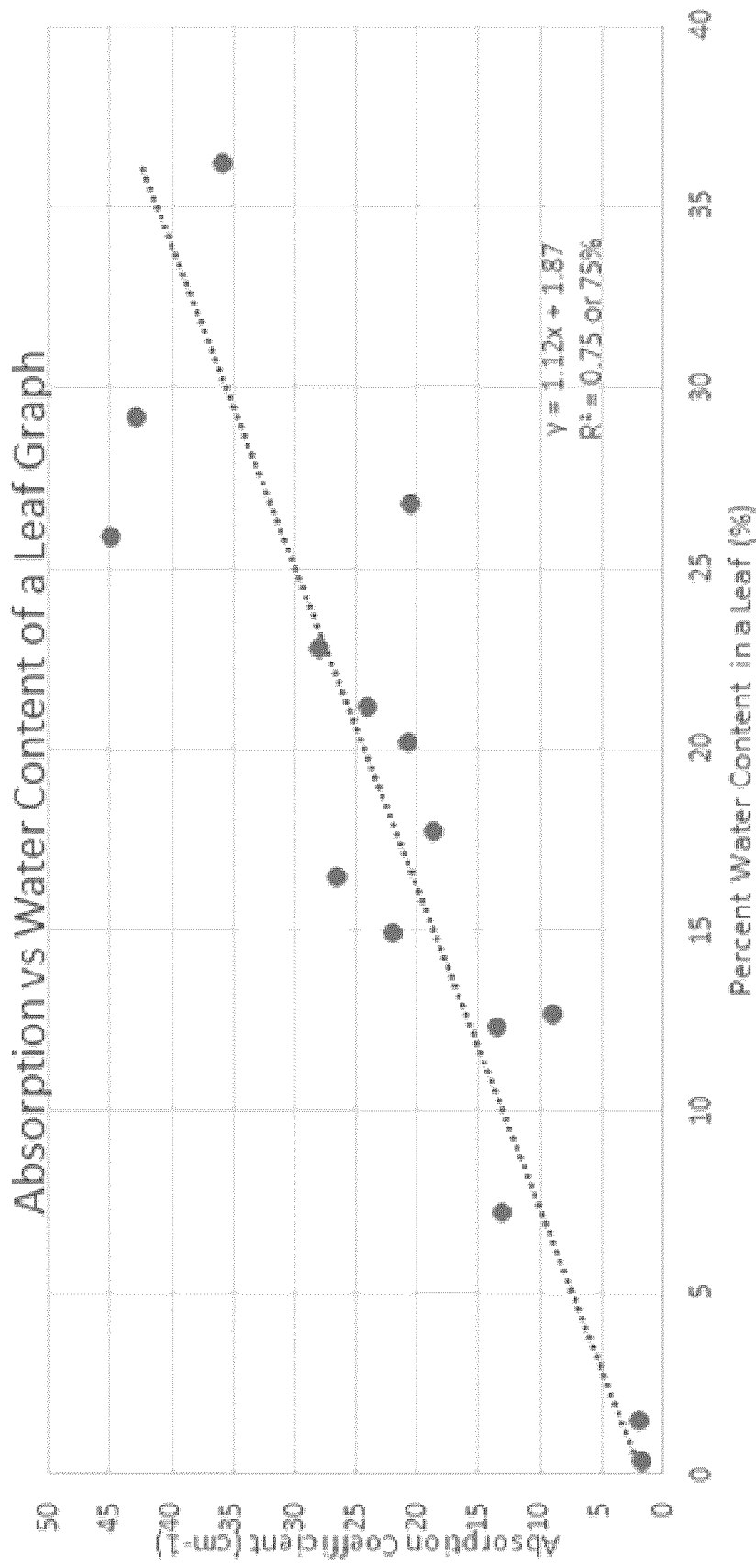
FIG. 17 shows a graph of the absorption coefficient of infrared radiation by a leaf at 1940 nm versus the percent water content in the leaf.

FIG. 17 shows a graph representing a linear trend line for all the data points for absorbance at 1940 nm of the three trials. The graph shows that the amount of water in the leaf is proportional to the absorption coefficient at 1940 nm. As the water content increases, the absorption coefficient also increases at 1940 nm. This experiment demonstrates that the moisture content of a leaf can be determined based on the absorption coefficient of the leaf, including as determined at the wavelength 1940 nm.

For the *Peperomia* plants used in this example, the moisture content of the leaf was empirically determined as described above, and from the data presented in FIG. 17, it can be determined that the % moisture content of the leaf can be calculated based on the absorbance coefficient of the leaf at 1940 nm as follows from Equation (8):

$$\% \text{ Water Content} = \frac{\text{Absorbent } Coeff_{1940}}{1.12} - 1.67 \quad (8)$$

Thus, for *Peperomia* plants, the percentage moisture content of the leaf can be determined based on a determination of the absorption coefficient of the leaf at 1940 nm. This information can then be used to determine if the moisture content of the leaf is above or below a predetermined threshold that is considered acceptable based on the type of plant and the prevailing environmental conditions, wherein a determination that the moisture content of the leaf is below the predetermined threshold indicates a need to supply water to the plant, while a determination that the moisture content of the leaf is at or above the predetermined threshold indicates that additional water does not need to be supplied.

Similar experiments could be conducted for other types of plants or using the plant canopy in specific growing settings to derive an equation relating the absorbance coefficient or other IR parameter as determined at 1940 nm or at a band of wavelengths centered at approximately 1940 nm to the moisture content (i.e. % water content) in the plant. The moisture content of the plant as determined by the measured absorbance coefficient can then be used as a control parameter, to determine for example when an irrigation system should be activated to supply water to the growing plants. This experiment demonstrates that the measured IR parameter of the plant part (i.e. the plant leaf) can be used to non-destructively evaluate the % water content of a leaf based on the measured IR value after a standard curve has been established.

Example 2.0—Description of Prophetic Example Embodiment of Calculating Plant Canopy Moisture Content and Biomass To illustrate how the foregoing principles are applied, in one example, a plant will be taken from a well-watered condition and soil will be dried to the permanent wilting point (PWP) while monitoring the IR spectrum, similar to the manner in which leaves were collected and then dried in Example 1.0. The changes in IR parameters, e.g. IR absorption or reflectance change at various wavelengths, due to stress experienced by the plant (e.g. by measuring changes in moisture content, biomass or cellulose content, levels of stress hormones and/or plant stress levels) will then be quantified and used as an input to a control algorithm and/or alarmed (i.e. configured to trigger a perceptible alarm, including an audible, visual or electronically outputted alarm indicating that the plant or plant canopy are experiencing a stress condition). Further increases in stress from initial onset would increase the stress hormone levels; this would be analogous to the application of IR spectrometry for detecting the thickness of the latex application on paper (e.g. as per U.S. Pat. No. 5,795,394).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

All references, patents and published patent applications mentioned herein are specifically incorporated by reference in their entireties.

The invention claimed is:

1. A method of determining a health parameter of a plant comprising:

using a measuring device, measuring an infrared (IR) parameter of the plant to provide a measured IR parameter at a measuring wavelength at which the IR parameter is sensitive to variations in the health parameter;

using a measuring device, measuring a reference parameter of the plant at a reference wavelength at which the measured IR parameter exhibits no or limited variation with variations in the health parameter;

using a processor, comparing the measured IR parameter with the reference parameter to determine a relation between the measured IR parameter and the reference parameter; and using a processor, quantifying the health parameter of the plant based on the relation between the measured IR parameter and the reference parameter.

2. A method as defined in claim 1, wherein the health parameter of the plant comprises biomass, cellulose content, water content, a level of a compound that is indicative of stress, or a level of one or more of water, nitrogen, phosphorus, potassium, abscisic acid, cellulose or chlorophyll.

3. A method as defined in claim 1, wherein the health parameter of the plant is quantified by calibrating the relation between the measured IR parameter and the reference parameter with a standard curve to quantify the health parameter of the plant, wherein the standard curve is prepared by correlating the measured IR parameter to the health parameter of the plant at a plurality of different known plant stress levels; wherein optionally the health parameter is percentage water content and the standard curve is prepared by measuring the IR parameter for a plurality of leaves or plants at a plurality of different known moisture contents.

4. A method as defined in claim 1, wherein, at the reference wavelength, the measured IR parameter exhibits a maximum variation with variations in the health parameter that is less than 20%, less than 10% or less than 5% of a maximum variation of the IR parameter with variations in the health parameter at the measuring wavelength; and/or wherein the measured IR parameter is determined at the measuring wavelength at which an element associated with the health parameter absorbs infrared radiation.

5. A method as defined in claim 1, wherein the measured IR parameter is determined across a first path having a first length, and wherein the reference parameter comprises the IR parameter determined across a second path having a second length, wherein the first length and the second length are approximately the same, and wherein the first path comprises a plant canopy, a plant or a plant part, and wherein the second path comprises only air.

6. A method as defined in claim 1, wherein:
the health parameter is percentage water content, and the measured IR parameter is determined at a wavelength or a band of wavelengths centred at approximately 1940 nm;
the health parameter is abscisic acid content, and the measured IR parameter is determined at a wavelength or a band of wavelengths centred at approximately 5800 to 6250 nm;
the health parameter is nitrogen content, and the measured IR parameter is determined at a wavelength or a band of wavelengths centred at approximately 7.4 to 10 microns;
the health parameter is phosphorous content, and the measured IR parameter is determined at a wavelength or a band of wavelengths centred at approximately 7000 to 8000 nm;
the health parameter is potassium content, and the measured IR parameter is determined at a wavelength or a band of wavelengths centred at approximately 2450 to 2470 nm;
the health parameter is cellulose content, and the measured IR parameter is determined at a wavelength or a band of wavelengths centred at approximately 800 to 1300 nm; and/or
the health parameter is chlorophyll content, and the measured IR parameter is determined at a wavelength or a band of wavelengths centred at approximately 400 to 800 nm.

7. A method as defined in claim 6, wherein the health parameter is percentage water content, and wherein the reference parameter is the IR parameter determined at a wavelength or a band of wavelengths centred at approximately 1700 nm.

8. A method of controlling environmental conditions based on plant health, the method comprising:
carrying out a method as defined in claim 1 to determine a health parameter of a plant;
using a processor, evaluating whether the health parameter indicates that the plant is experiencing a stress condition; and
using a processor, providing a perceptible indication to an operator that the plant is experiencing a stress condition, and/or activating a controller to supply one or more elements to the plant to ameliorate the stress condition;
wherein optionally the stress condition is a lack of water, and wherein activating the controller comprises activating an irrigation system to supply water to the plants, optionally where in the controller comprises a proportional-integral-derivative controller that can regulate activation and de-activation of the irrigation system based on continued monitoring of the plant health parameter.

9. A method of measuring a plant health parameter comprising one or more of: a level of moisture in a plant canopy, a biomass of a plant canopy, a cellulose content of a plant canopy and a level of stress of plants comprising a plant canopy, the method comprising:
using a measuring device, measuring a measured infrared (IR) parameter value at a measuring wavelength at which the measured IR parameter value is sensitive to variations in the plant health parameter for a measuring path extending through the plant canopy;
using a processor, comparing the measured IR parameter value with the reference IR parameter value to determine a relation between the measured IR parameter value and the reference IR parameter value; and
using a processor, determining one or more of: the level of moisture in the plant canopy, the biomass of the plant canopy, the cellulose content of the plant canopy, and the level of stress of the plants comprising the plant canopy based on the relation between the measured IR parameter value and the reference IR parameter value.

10. A method as defined in claim 9, wherein the reference IR parameter value is determined by measuring the IR parameter of a control sample, optionally wherein the control sample comprises dried plant leaves or a dried plant.

11. A method as defined in claim 9, wherein:
the measuring wavelength is a wavelength at which a material of interest to assess health absorbs infrared radiation to a first degree, the reference IR parameter value is determined at a reference wavelength, and the reference wavelength is a wavelength at which a material of interest to assess health absorbs infrared radiation to a second degree, wherein the first degree is at least ten times higher than the second degree; and/or
the measured IR parameter value is determined at a wavelength at which a material of interest to assess health absorbs infrared radiation.

12. A method as defined in claim 9, wherein:
the material of interest comprises water, abscisic acid, potassium, nitrogen, phosphorus, cellulose, biomass or chlorophyll;
the material of interest comprises water, and the first wavelength is approximately 1940 nm and the second wavelength is approximately 1700 nm;

the material of interest comprises water, and wherein the measured IR parameter value is determined at a wavelength or band of wavelengths centred at approximately 1940 nm;

the material of interest comprises abscisic acid, and wherein the measured IR parameter value is determined at a wavelength or band of wavelengths centered at approximately 5800 to 6250 nm;

the material of interest comprises potassium, and wherein the measured IR parameter value is determined at a wavelength of approximately 2450 to 2470 nm;

the material of interest comprises nitrogen, and wherein the measured IR parameter value is determined at a wavelength or band of wavelengths centred at approximately 7.4 to 10 microns;

the material of interest comprises phosphorus, and wherein the measured IR parameter value is determined at a wavelength or band of wavelengths centered at approximately 7000 to 8000 nm;

the material of interest comprises chlorophyll, and wherein the measured IR parameter value is determined at a wavelength or band of wavelengths centred at approximately 400 to 800 nm;

the material of interest comprises cellulose, and wherein the measured IR parameter value is determined at a wavelength or band of wavelengths centred at approximately 800 to 1300 nm; and/or the material of interest comprises biomass, and wherein the measured IR parameter value is determined at a wavelength of approximately 800 to 1300 nm.

13. A method as defined in claim 9, wherein:

the measured IR parameter value and the reference IR parameter value comprise absorption, transmission or reflectance;

the measured IR parameter value and the reference IR parameter value comprise absorption coefficients;

the plant canopy comprises one plant; or the plant canopy comprises a row of plants.

14. A method as defined in claim 9, wherein the plant canopy comprises a plurality of rows of plants, wherein the step of measuring a measured IR parameter value comprises:

(a) measuring the measured IR parameter value for a measuring path extending through a first one of the plurality of rows of plants;

(b) moving the apparatus used to measure the IR parameter value horizontally to a second one of the plurality of rows of plants; and (c) measuring the measured IR parameter value for a measuring path extending through the second one of the plurality of rows of plants; and (d) repeating steps (b) and (c) for each remaining one of the plurality of rows of plants.

15. A method as defined in claim 14, wherein the plant canopy comprises a plurality of tiers of plants, wherein the step of measuring a measured IR parameter comprises:

(e) measuring the measured IR parameter value for a measuring path extending through a first one of the plurality of tiers of plants;

(f) moving the apparatus used to measure the IR parameter value vertically to a second one of the plurality of tiers of plants; and (g) measuring the measured IR parameter value for a measuring path extending through the second one of the plurality of tiers of plants; and (h) repeating steps (f) and (g) for each remaining one of the plurality of tiers of plants.

16. A method as defined in claim 9, wherein an average level of one or more of: the level of moisture in the plant canopy, the biomass of the plant canopy, the cellulose content of the plant canopy, and the level of stress of the plants comprising the plant canopy is determined by measuring the measured IR parameter value for a plurality of different measuring paths extending through the plant canopy at a plurality of different elevations.

17. A method of controlling growth conditions for a plant canopy, the method comprising:

measuring a health parameter comprising one or more of: the level of moisture in a plant canopy, the biomass of a plant canopy, the cellulose content of a plant canopy and the level of stress of plants comprising a plant canopy by carrying out a method as defined in claim 9; and adjusting conditions under which the plant canopy is being grown based on changes in one or more of: the level of moisture in a plant canopy, the biomass of a plant canopy, the cellulose content of a plant canopy and the level of stress of plants comprising a plant canopy, wherein optionally the step of adjusting the conditions under which the plant canopy is being grown comprises adjusting one or more of temperature, moisture supplied to roots of the plant canopy, humidity, light, or carbon dioxide supplied to the plant canopy.

18. A method of alarming growth conditions for a plant canopy, the method comprising:

measuring a health parameter comprising one or more of: the level of moisture in a plant canopy, the biomass of a plant canopy, the cellulose content of a plant canopy and the level of stress of plants comprising a plant canopy by carrying out a method as defined in claim 9;

determining whether the measured values for one or more of: the level of moisture in a plant canopy, the biomass of a plant canopy, the cellulose content of a plant canopy and the level of stress of plants comprising a plant canopy indicates that the plant canopy is experiencing a stress condition; and providing a perceptible indication if it is determined that the plant canopy is experiencing a stress condition, wherein the step of providing a perceptible indication optionally comprises providing an audible or visible alarm or moving a visible indicator from a first position indicating that the plant canopy is experiencing acceptable growing conditions to a second position indicating that the plant canopy is experiencing stress conditions.

19. A method as defined in claim 9, wherein:

the measured IR parameter is determined at a band of infrared radiation centred at approximately 1.94 micrometers, and wherein the level of moisture in the plant canopy is determined;

the reference IR parameter is determined at a band of infrared radiation centred at approximately 1.7 micrometers, and wherein one or both of the level of biomass of the plant canopy and the cellulose content of the plant canopy is determined; and/or the measured IR parameter are determined using infrared radiation having a wavelength of between 0.5 micrometers and 10 micrometers.

20. An apparatus for measuring a health parameter, the apparatus comprising:

a measuring IR source for emitting radiation at a measuring wavelength;

a measuring IR detector for measuring a measured infrared (IR) parameter at the measuring wavelength at which the measured IR parameter is sensitive to variations in the health parameter;
a reference IR source for emitting radiation at a reference wavelength at which the measured IR parameter exhibits no or limited variation with variations in the health parameter;
a reference IR detector for measuring a reference parameter at the reference wavelength; and
a controller programmed to compare the measured IR parameter to the reference parameter and quantify the health parameter of the plant based on a relation between the measured IR parameter and the reference parameter.

* * * * *